(12) United States Patent
Yeh et al.

(10) Patent No.: US 10,000,766 B2
(45) Date of Patent: Jun. 19, 2018

(54) RECOMBINANT CONSTRUCT, RECOMBINANT MICROORGANISM, RECOMBINANT PLANT CELL AND METHOD OF PROVIDING PLANT WITH RESISTANCE AGAINST DNA VIRUS AND RNA VIRUS

(71) Applicant: NATIONAL CHUNG HSING UNIVERSITY, Taichung (TW)

(72) Inventors: Shyi-Dong Yeh, Taichung (TW); Ching-Fu Yang, New Taipei (TW); Kuan-Chun Chen, Taichung (TW); Ya-Ling Huang, Changhua (TW)

(73) Assignee: NATIONAL CHUNG HSING UNIVERSITY, Taichung (TW)

( * ) Notice: Subject to any disclaimer, the term of this patent is extended or adjusted under 35 U.S.C. 154(b) by 172 days.

(21) Appl. No.: 14/802,614

(22) Filed: Jul. 17, 2015

(65) Prior Publication Data

US 2017/0016021 A1    Jan. 19, 2017

(51) Int. Cl.
  *C12N 15/82*     (2006.01)
(52) U.S. Cl.
  CPC ..... *C12N 15/8283* (2013.01); *C12N 15/8218* (2013.01)

(58) Field of Classification Search
  None
  See application file for complete search history.

(56) References Cited

U.S. PATENT DOCUMENTS 8,168,774 B2 *   5/2012  Graham ................ A61K 48/00
                                                  536/24.5

* cited by examiner

*Primary Examiner* — Elizabeth F McElwain
(74) *Attorney, Agent, or Firm* — Muncy, Geissler, Olds & Lowe, P.C.

(57) ABSTRACT

Provided is a strategy for generating transgenic plants with concurrent resistance to DNA and RNA viruses at one construction, so as to develop an RNA-directed DNA methylation (RdDM) transgenic system using a hairpin construct of Ageratum yellow vein virus (AYVV) promoter region residing in an intron to resist DNA virus infection by RdDM. Furthermore, the hairpin construct of the AYVV promoter region coupled with an untranslatable nucleocapsid protein (NP) fragment of Melon yellow sport virus (MYSV) is created to induce post-transcriptional gene silencing (PTGS) against MYSV. A method for providing transgenic plants conferring concurrent resistance to both AYVV and MYSV for control of DNA and RNA virus at the same time, and underlying RdDM and PTGS mechanisms, respectively, is also provided.

11 Claims, 9 Drawing Sheets

RECOMBINANT CONSTRUCT, RECOMBINANT MICROORGANISM, RECOMBINANT PLANT CELL AND METHOD OF PROVIDING PLANT WITH RESISTANCE AGAINST DNA VIRUS AND RNA VIRUS

BACKGROUND OF THE INVENTION

1. Field of the Invention

This invention relates to a recombinant construct for providing a plant with resistance against a DNA virus and a RNA virus and a method thereof through the siRNA-mediated pathway, and the recombinant construct cannot be expressed as a protein product in plant.

2. Description of the Related Art

Global threats of crop diseases caused by virus have led to tremendous economic losses. For example, the ssDNA geminiviruses, which infect covering monocotyledons and dicotyledons, cause the crop diseases such as beet curly top, cassava mosaic, cotton leaf curl, maize streak and tomato leaf curl. The ssRNA tospovirus, which can infect a wide range of hosts, have been documented infecting over nine hundred different plant species from 82 different families.

The different genetic structures and molecular mechanisms of geminiviruses and tospoviruses necessitate applications of transcriptional gene silencing (TGS) and post-transcriptional gene silencing (PTGS), respectively, for their control. Both TGS and PTGS depend on small interfering RNAs (siRNA) or microRNAs (miRNA) that are produced from double-stranded RNA (dsRNA) precursors. TGS occurs in nuclei via RNA-directed DNA methylation (RdDM) at CG, CHG and CHH sequence contexts (where H=A, T or G), whereas PTGS operates in the cytoplasm through mRNA cleavage or inhibition of translation.

PTGS-mediated transgenic resistance has been well applied for the control of plant RNA viruses, including tospoviruses, however, in the case of ssDNA geminiviruses, most attempts using PTGS approach have only resulted in short delay in symptom development or reduced disease severity.

On the other hand, the transgenic plants may carry a marker gene such as antibiotic resistant genes or herbicide resistant genes or the like. However, the marker gene may be expressed as proteins in plant, and such approach may cause potential risks to ecology and is also concerns for food safety.

Therefore, it is a primary issue to provide a plant that has resistances against DNA virus and RNA virus both, and the foreign gene may not be expressed as a foreign protein in plant.

SUMMARY OF THE INVENTION

The present invention provides a recombinant construct for providing a plant with resistances against a DNA virus and a RNA virus, and a method of using the recombinant construct to obtain a plant have resistance against the DNA virus and the RNA virus, and the marker-free transgenic plant can be selected in segregation.

To achieve the foregoing objective, the present invention provides a recombinant construct for providing resistance against the DNA and RNA virus to a plant. The recombinant construct comprises an intron region and an exon region. The intron region inserted in the exon comprises a fragment of an intergenic region sequence from a flanking sequence in a promoter region of a DNA virus, a spacer sequence and an antisense sequence of the fragment of the intergenic region sequence, the spacer sequence linked between the fragment of the intergenic region sequence and the antisense sequence of the fragment of the intergenic region sequence. The exon region comprises at least a fragment of a nucleocapsid protein gene of a RNA virus, and the nucleocapsid protein gene comprising at least a stop codon at 5' end.

Preferably, the nucleocapsid protein gene comprises at least two stop codons at 5' end.

Preferably, the fragment of the intergenic region sequence may consist of a sequence of SEQ ID NO: 1.

Preferably, the intron region may comprise a sequence of SEQ ID NO: 2.

Preferably, the recombinant construct further comprises a binary vector containing a first control sequence and a second control sequence, and the intron region and the exon region are operably linked to the first control sequence.

Preferably, the first control sequence contains a promoter and a terminator, and the intron region and the exon region are located between the promoter and the terminator, and no selectable marker gene exists is located in the first control sequence.

Preferably, the promoter of the binary vector comprises a Cauliflower Mosaic Virus 35S promoter, a Cauliflower mosaic virus double 35S promoter or an ubiquitin promoter.

Preferably, the DNA virus comprises Ageratum yellow vein virus or Tomato yellow leaf curl virus.

Preferably, the RNA virus comprises Melon yellow sport virus or Watermelon silver mottle virus.

To achieve the foregoing objective, the present invention provides a recombinant microorganism prepared by transforming a microorganism with the recombinant construct mentioned above.

Preferably, the microorganism comprises disarmed *Agrobacterium tumefaciens*.

To achieve the foregoing objective, the present invention provides a recombinant plant cell with resistances against a DNA virus and a RNA virus. The recombinant plant cell comprises a genome comprising the recombinant construct mentioned above.

Preferably, the recombinant plant cell is free of a marker gene.

Preferably, the marker gene is selected from a group consisted of an antibiotic resistance gene, an herbicide resistant gene and a fluorescent protein gene.

To achieve the foregoing objective, the present invention provides a method of providing a plant with resistance against a DNA virus and a RNA virus, and the method comprises a step of introducing the recombinant construct mentioned above into a plant or plant part, wherein a siRNA is generated from the intron region of the recombinant construct, to induce RNA-directed DNA methylated in the promoter region of the DNA virus to provide the resistance against the DNA virus in the plant, wherein the exon region of the recombinant construct is expressed in a transcript but not translationally expressed in cytoplasm, and induce the post-transcriptional gene silencing to provide resistance against the RNA virus in plant.

Preferably, the method mentioned above further comprises steps of introducing the recombinant construct into an *Agrobacterium* sp. to obtain a recombinant *Agrobacterium* sp.; and infecting the plant or plant part with the recombinant *Agrobacterium* sp. to obtain a plant having the recombinant construct.

Compared with the traditional technology, the present invention has following advantages. First, the present invention develops one recombinant construction, which can be generated siRNA or miRNA after splicing, to induce RdDM and PTGS process to provide transgenic plants with resistance against the DNA virus and the RNA virus. Second, the binary vector is used in this invention, and the recombinant construction is inserted into one of the control sequence of the binary vector, and the marker gene is inserted into the other of the control sequence of the binary vector, so the transgenic plant containing the marker gene can be selected and be segregated. Therefore, the selected transgenic plant cannot express the foreign protein from the coding sequence of recombinant construction, so the potential risks of foreign protein presence are lower.

BRIEF DESCRIPTION OF THE DRAWINGS

FIG. 1 is a schematic diagram of constructions of the present invention. Abbreviations, LB: T-DNA left border; 2X355-P: Cauliflower mosaic virus (CaMV) double 35S promoter; marked (**): stop codons; MY-: 59 part of MYSV-NP coding sequence; AT-In-: 59 part of the intron of gene At3947160 of *Arabidopsis thaliana*; IGR: fragment of the intergenic region (IGR) flanked by 54 bp of C1 gene at the right (filled with slant line) and 56 bp of V2 gene at the left (filled with dots) of Ageratum yellow vein virus (AYVV); spacer: a 96 bp fragment of the middle part of the At3947160 intron; Inverted IGR: the fragment of the inverted IGR repeat of AYVV; -tron: 39 part of the At3947160 intron; -SV-NP: 39 part of the MYSV-NP coding sequence; 355-T: CaMV 35S terminator; RB: T-DNA right border; nos-P: nopaline synthase gene promoter; nptII: neomycin phosphotransferase gene; nos-T: nos terminator. pK2T-MY-intron-NP: A positive control for confirmation of the action of the splicing process.

FIG. 2 is an analysis of the splicing of individual constructs in tobacco leaves. The lines 1-3 of RT-PCR are samples extracted at 3 dpi from tobacco leaves agroinfiltrated with individual constructs of pK2T-MYSV-NP, pK2T-MY-intron-NP and pK2T-MY-int-hpIGR-NP to examine the splicing of the intron. The lines 1-3 of Genomic DNA are samples extracted from the leaf tissues agroinfiltrated as unspliced controls.

FIG. 3 shows symptom of the individual tobacco plant at 27 days post-agroinfection with the infectious construct pAYVV. Abbreviations, NT: non-transgenic plant; Mock: a NT plant inoculated with buffer; MY-int-hpIGR-NP-6, hpIGR-3 and IGR-2 indicate transgenic lines transformed with the constructs pK2T-MY-int-hpIGR-NP, pK2T-hpIGR and pK2T-IGR, respectively.

FIG. 4, part (b), shows the result of FIG. 4 part (a) in high resolution. Different resistant (R) lines showed different days (the number in parentheses) of delay in symptom development are used for Northern blot analysis. Ribosomal RNA (5S) and tRNA are used as loading controls, and S refer to susceptible line.

Figure 6:
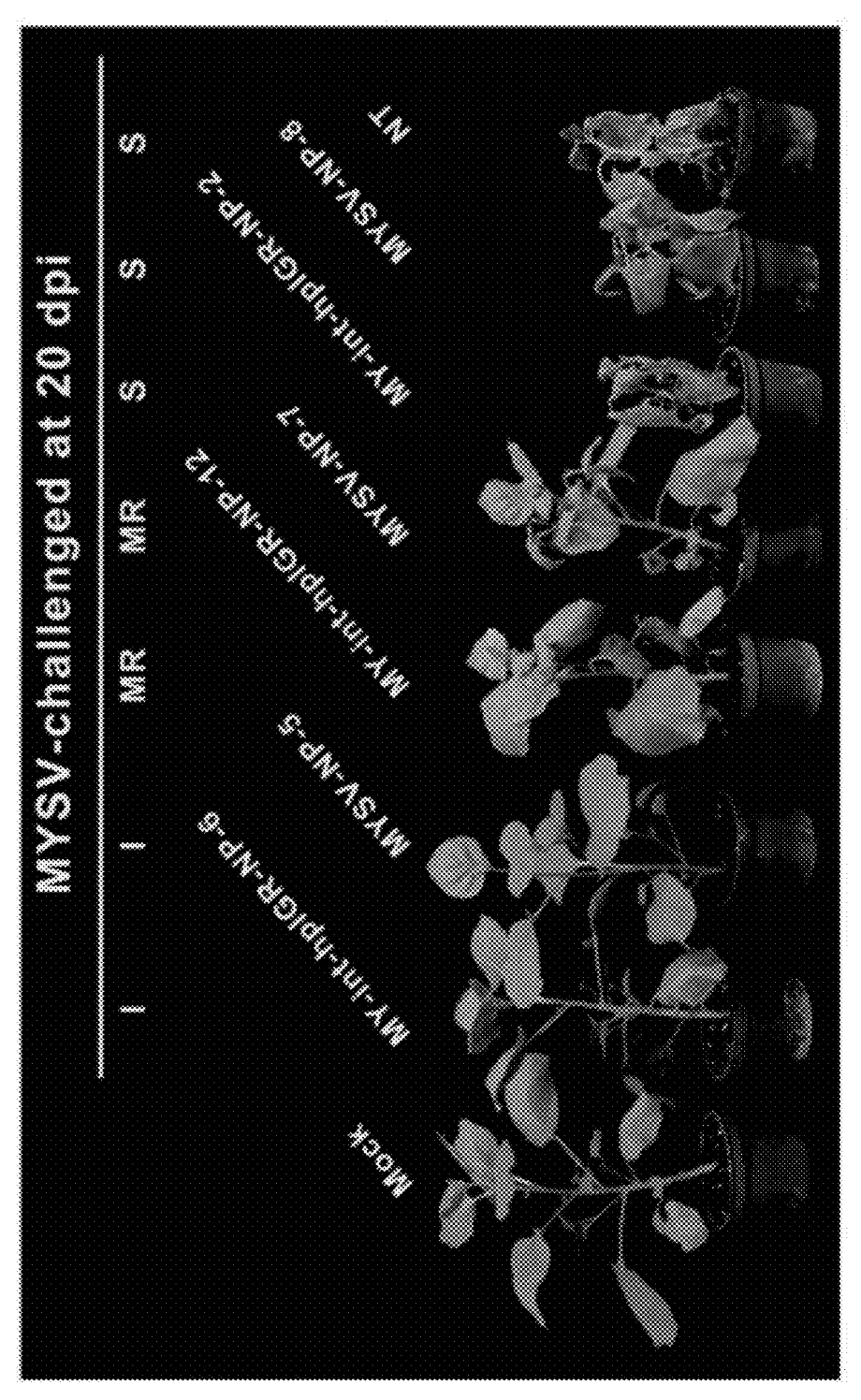

FIG. 6 shows a symptom of transgenic MY-int-hpIGR-NP and MYSV-NP lines by mechanical inoculation with MYSV. Abbreviations, I: immune resistant; MR: moderately resistant; S: susceptible.

FIG. 7 shows the detection of MYSV-NP transcript and siRNAs in MY-int-hpIGR-NP and MYSV-NP lines.

DETAILED DESCRIPTION OF THE PREFERRED EMBODIMENTS

Figure 4:
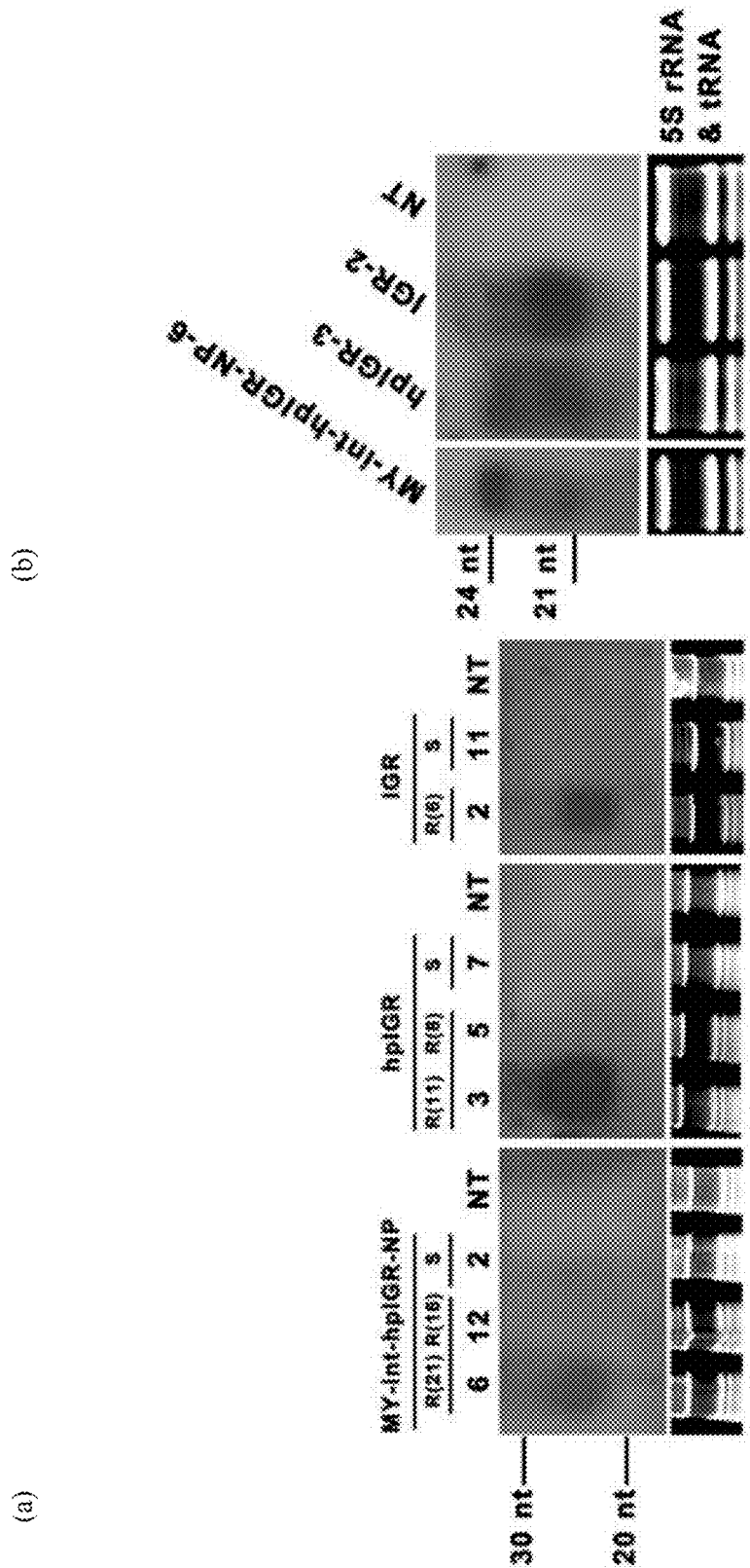
FIG. 4, part (a), shows the detection of the siRNAs accumulation in plant related with AYVV resistant.
Figure 5:
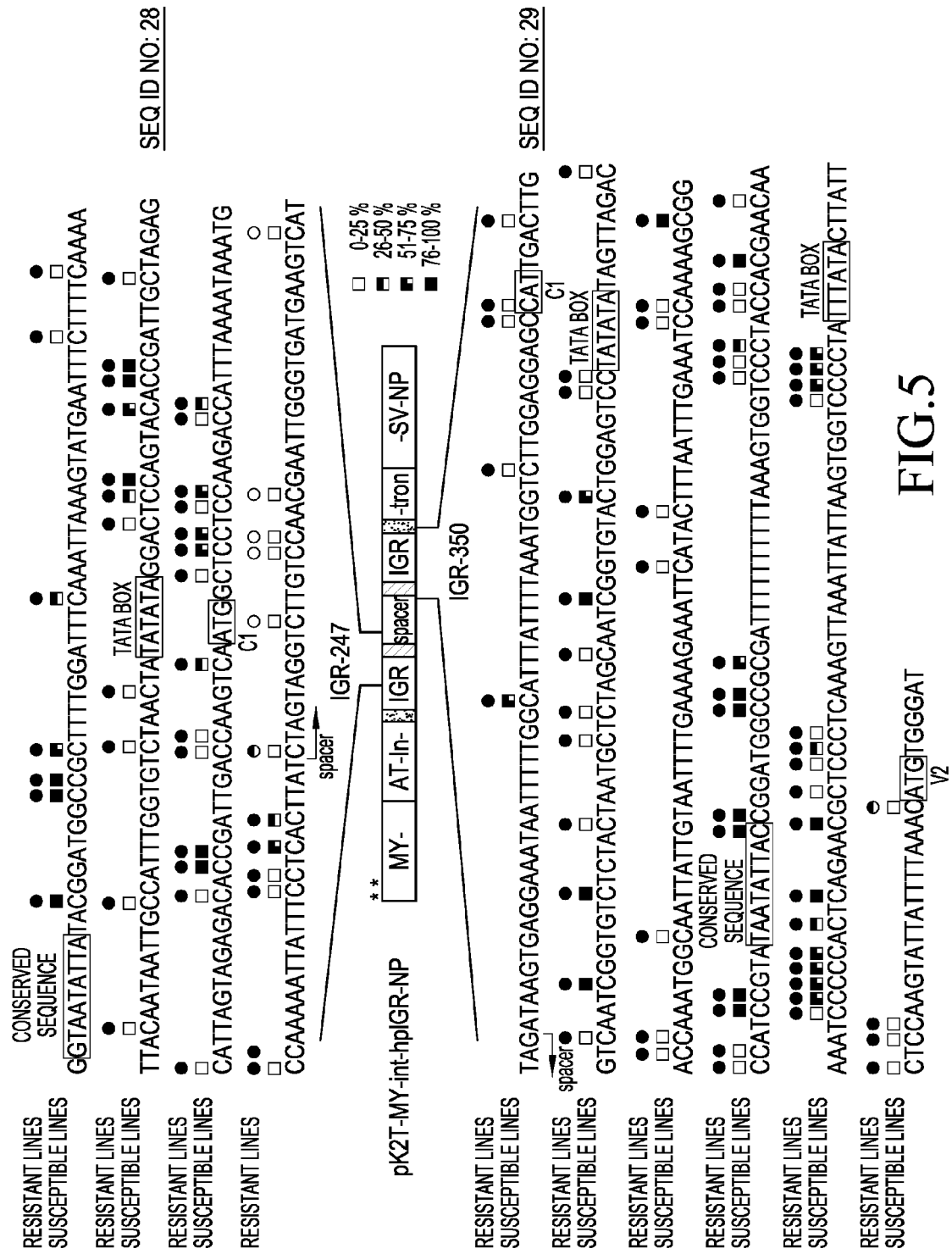
FIG. 5 is a physical map of the MY-int-hpIGR-NP transgene, in which the regions analyzed by bisulfate sequencing are indicated. The 247 bp (IGR-247) (SEQ ID NO: 28) and the 350 bp (IGR-350) (SEQ ID NO: 29) fragments are analyzed by the primer pairs BisP1/BisM1 and BisP2/BisM2, respectively. Circles indicate sites of methylation identifies from resistant MY-int-hpIGR-NP lines (6 and 12), and squares indicate sites of methylation identifies from the susceptible MY-int-hpIGR-NP lines (2 and 19). Open circles (for resistant lines) and squares (for susceptible lines) represent 0-25% methylation of cytosines, half-filled symbols 26-50%, three-quarters-filled symbols 51-75% and full-filled symbols 76-100%. Sequencing data are averaged from three repeats. TAATATT↓AC: the conserved replication origin; TATA box: an essential motif of predicted promoter, translation start sites of C1 and V2 ORFs are also boxed.

A recombinant construct, which can provide resistance against the DNA and RNA viruses to a plant, comprises an intron region and an exon region. The intron region comprises a fragment of an intergenic region (IGR) sequence, a spacer sequence and an antisense sequence of the fragment of the intergenic region sequence, and the spacer sequence linked between the fragment of the intergenic region sequence and the antisense sequence of the fragment of the intergenic region sequence, in this present invention, the fragment of the intergenic region (IGR) refer to a sequence isolated from a flanking sequence in a promoter region of a DNA virus. The exon region comprises at least a fragment of a nucleocapsid protein gene of a RNA virus, and the intron region is inserted in the exon region.

In splicing, the mRNA coding from the intron region generates a hairpin structure through complementation of the fragment of IGR sequence and the antisense sequence of the same after the mRNA coding form the intron region is cutoff from the pre-mRNA coding form the recombinant construct. Then, the 24-nt small-interfering RNA (siRNA) is processed from the double-stranded RNA (dsRNA) of the hairpin structure formed by Dicer-like 3 (DCL3) in plant nucleus, and predominantly loaded into Argonaute 4 (AGO4) to guide RNA-directed DNA methylation (RdDM) pathway.

The term "small-interfering RNA (siRNA)" or "siRNA-directed DNA methylation (RdDM)" refers to an intron gene generated a hairpin structure RNA in nucleus to induce the RdDM pathway. That is, the hairpin structure RNA coding IGR sequence can be accumulated in nucleus, and the siRNA can be generated by DCL3 to induce RNA-directed DNA methylated in the homologous DNA sequence. In this present invention, the siRNA can induce the methylation nearby the promoter of DNA virus, so the downstream gene of promoter cannot be transcribed and it causes the plant to have the resistance against DNA virus.

The IGR sequence of the present invention comes from a fragment of the IGR sequence of promoter region of Ageratum yellow vein virus (AYVV), however, the IGR sequence can be replaced by appropriate sequences for effective control of other geminiviruses or any other DNA viruses, for example, an AYVV IGR sequence (accession no.: AB100305) or an IGR sequence (accession no.: GU178818) of Tomato yellow leaf curl virus (TYLCV) can make a plant have resistance against the TYLCV virus; however, the present invention is not limit thereto.

The intron region of the present invention comprises an intron sequence which can be spliced in plant cell, and according to plants or crops for transformation the intron sequence can be replaced, for example, an intron sequence of the *Arabidopsis thaliana* (accession no.: AL133292.3) to transform the *N. benthamiana* plants, an intron sequence of the tomato (accession no.: L25128) to transform the tomato plant; however, the present invention is not limit thereto.

The exon region is expressed in a transcript but not translationally expressed in cytoplasm, so as to induce the post-transcriptional gene silencing. The intron region is inserted into the exon region, and an mRNA of the exon region is generated in splicing. The exon region may be modified by any means to prevent expression of protein corresponding to the coding sequence fragment; and preferably, by inserting at least one stop codon at 5' end or including a reading frame shift.

The term "untranslational expression" or "not translationally expressed" refers to allow a gene being expressed before the stage of gene translation by any means, that is, no complete protein is expressed. Therefore, means therefor may include providing a coding sequence fragment having a reading frame shift or inserting a stop codon into the coding sequence fragment, which results in producing transgene transcripts but not proteins of the transgene. The transcripts will be degraded into small interfering RNA (siRNA), no transgene transcripts but a great amount of fragments of siRNA are detected in transgenic lines with resistance against virus.

The exon region of the present invention comprises a coding sequence of at least a fragment of the nucleocapsid protein (NP) gene of the Melon yellow sport virus (MYSV) RNA virus, to make the plant have a resistance against to MYSV RNA virus. Similarly, the exonic MYSV NP sequence can be replaced by appropriate sequences for effective control of other tospoviruses or any other RNA viruses, for example, the MYSV NP gene (accession no.: FJ386391.1) or at least a fragment of the NP gene (accession no.: AY514627.1) of Watermelon silver mottle virus (WSMoV) for providing a plant to against the WSMoV RNA virus; however, the present invention is not limit thereto.

The recombinant construct mentioned above can be inserted into a binary vector containing a control sequence, and the intron region and the exon region are operably linked to the control sequence.

As known in the art, the binary vector refers to a cloning vector for generating a transgenic plant, having ability to be amplified in *Escherichia coli* and *Agrobaclerium tumefaciens*. In this present invention, the binary vector is pK2T which has two T-DNA cassettes, one of the T-DNA cassettes contains a Cauliflower mosaic virus (CaMV) 35S promoter and 35S terminator, the other of the T-DNA cassettes contains nopaline synthase (Nos) promoter and Nos terminator. Preferably, the recombinant construct is located between CaMV 35S promoter and 35S terminator, a selectable marker gene is located between Nos promoter and Nos terminator.

The term "control sequence", as used herein, refers to a sequence capable of switching on or off a gene or fragment thereof to regulate expression of the gene or fragment thereof, such as a promoter or terminator. For example, the promoter comprises a CaMV 35S promoter, a CaMV double 35S promoter or an ubiquitin promoter, but no limit to.

The term "operably linked" refers to expression of a gene controlled by a spatially linked control sequence. The control sequence may be at 5' end (upstream) or 3' end (downstream) of the gene controlled by the control sequence. As known in the art, distance between control sequence and the gene can be adjusted without influencing function of the control sequence.

The selectable marker gene of the present invention comprises an antibiotic resistance gene, an herbicide resistant gene or a fluorescent protein gene, for example, a kanamycin resistant gene (nptII gene), but the present invention is not limited thereto. Preferably, the selectable marker gene is not located on the same T-DNA cassette of the recombinant construct.

A recombinant microorganism in accordance with the present invention is prepared by transforming a microorganism with the recombinant construct as described above. Preferably the microorganism preferably is bacterium, more preferably, disarmed *Agrobaclerium tumefaciens*. In this present invention, the disarmed *Agrobaclerium tumefaciens* refers to *Argrobaclerium tumefaciens* containing vir genes and T-DNA, but no oncogenes of *Agrobacterium* sp.

In this present invention, a method of providing a plant with resistance against a DNA virus and a RNA virus comprises steps of introducing the recombinant construct into an *Agrobacterium* sp. to obtain a recombinant *Agrobacterium* sp.; and infecting the plant or plant part with the recombinant *Agrobacterium* sp. to obtain a plant having the recombinant construct.

The terms "introduce" and "transfer" are alternatively used and refer to bringing a nucleic acid fragment, plasmid and the like into cells by any known transformation techniques in the art.

According to this method, a recombinant plant with the recombinant construct described above can be generated. Because the recombinant construct and the selectable marker gene are located in different T-DNA cassette, these two T-DNA cassettes can be inserted into different genomic loci of transgenic plant, therefore, these two T-DNA cassettes can be separated during meiosis, and the recombinant construct or/and the selectable marker gene can present in next generation, that is, a marker free transgenic plant can be selected form $T_1$ plants, and the selected transgenic plant cannot expressed the foreign protein from the selectable marker gene.

Examples

The primer list used in the present invention is showed in Table 1.

TABLE 1

Primer list

| Purpose | SEQ ID NO | Primer name | Sequence from 5' to 3' |
|---|---|---|---|
| Plasmid | 6 | P-AT int-Nde I | CACCATATGTAAGCCTCTCAAATTTGATTCC |
| | 7 | M-AT int-Nhe I | GCTAGCTGTTAATTCACAGAGGAGAAAC |
| | 8 | P-inBsSp | GGTTTAAGTGGGTTTCCGGAACTAGTAGGTCTTGTCCAA |
| | 9 | M-inBsSp | TTGGACAAGACCTACTAGTTCCGGAAACCCACTTAAACC |

TABLE 1-continued Primer list

| Purpose | SEQ ID NO | Primer name | Sequence from 5' to 3' |
|---|---|---|---|
| | 10 | P-IGR-Xba I | CACCTCTAGATAAGTGAGGAAATAATTTTTG |
| | 11 | M-IGR-Xma I | CCCGGGCATACACCTAAAACCGTGAACAG |
| | 12 | P-inAvBs | TGAAGCTGAACAAAGCCTAGGTCCGGATGAT CTCAGAGGA |
| | 13 | M-inAvBs | TCCTCTGAGATCATCCGGACCTAGGCTTTGTT CAGCTTCA |
| | 14 | P-MYSV-Xba I | GTATCTAGAATGTAATAAGTTACTAAGCTGA CAAAGGAG |
| | 15 | M-MYSV-Xma I | AGGCCCGGGTTAAACTTCAATGGACTTAG |
| | 16 | M-spacer-Xba I | CTCTCTAGACTAGGCTTTGTTCAGCTTCAA |
| Bisulfite assay | 17 | BisP1 | GGTAATATTATAYGGATGGYYGYTTTTG |
| | 18 | BisM1 | CTACCTAAAAATRACTTCATCACCCAATTC |
| | 19 | BisP2 | TAGATAAGTGAGGAAATAATTTTTGG |
| | 20 | BisM2 | ATCCCACATRTTTAAAATAATACTTR |
| Southern blotting probe | 14 | P-MYSV-Xba I | GTATCTAGAATGTAATAAGTTACTAAGCTGA CAAAGGAG |
| | 21 | M-MYSV-N-350 | TCTTCTTCATTCTCTGTCTTTTCTGC |
| Northern blotting probe | 14 | P-MYSV-Xba I | GTATCTAGAATGTAATAAGTTACTAAGCTGA CAAAGGAG |
| | 15 | M-MYSV-Xma I | AGGCCCGGGTTAAACTTCAATGGACTTAG |
| npt II selection | 22 | P-kan | ACTCGTCAAGAAGGCGATAG |
| | 23 | M-kan | GCATGATTGAACAAGATGGA |
| confer AYVV infection | 24 | P-AYVV-C4 | GAACCCCTGAGGGAGCCCTCATCTCCACG |
| | 25 | M-AYVV-C4 | AGGGCTCCCTCAGGGGTTCTGTACATTCTG |
| Tobacco actin | 26 | P-NB-actin-413 | AACTGATGAAGATACTCACAGAAAGAGGC |
| | 27 | M-NB-actin-413 | CAGGATACGGGGAGCTAATGCAGTAATTT |

1. Construction of Target Genes in Two T-DNAs Binary Vector

An intron fragment of gene At3947160 of *A. thaliana* (accession number AL133292.3, bps 79239-78574) was amplified by PCR with the primer pair P-AT int-Nde I/M-AT int-Nhe I. The amplified fragment was digested with Nde I and Nhe I, and inserted into the vector pENTR™/D-TOPO (Invitrogen, Carlsbbad, Calif., USA) to generate pEN-intron. The pEN-intron was mutated with the primer pair P-inBsSp/M-inBsSp to create BspE I and Spe I sites at 130-141 bp of the intron, in which the fragment of the antisense intergenic region (IGR) of Ageratum yellow vein virus (AYVV) amplified by the primer pair P-IGR-Xba I/M-IGR-Xma I by PCR was introduced by Xma I/Xba I digestion to generate pEN-int-antiIGR. The construct pEN-int-antiIGR was mutated with the primer pair P-inAvBs/M-inAvBs to generate Avr II and BspE I sites at bps 622-633 of pEN-int-antiIGR, in which the fragment of the sense IGR of AYVV PCR-amplified with the primer pair P-IGR-Xba I/M-IGR-Xma I was introduced by Xba I/Xma I digestion to generate pEN-int-hpIGR, with a spacer of 96 bp from the middle part of the At3947160 intron.

An untranslatable nucleocapsid protein (NP) fragment of Melon yellow sport virus (MYSV), was amplified by RT-PCR from the total RNA extracted from a *N. benthamiana* plant infected with MYSV (accession number FJ386391.1) with the primer pair P-MYSV-Xba I/M-MYSV-Xma I, and introduced into Xba I/Xma I sites of the pCR 2.1-TOPO vector (Invitrogen, Carlsbbad, Calif., USA) to generate pTOPO-MYSV. The int-hpIGR fragment released from Nde I and Nhe I sites from pEN-int-hpIGR, was subsequently inserted to the pTOPO-MYSV to generate pTOPO-MY-int-hpIGR-NP, from which the MY-int-hpIGR-NP fragment was released by Xba I/Xma I digestion and introduced into the pk2T binary vector to generate pk2T-MY-int-hpIGR-NP.

In addition to the above construct that was attempted to induce both RdDM and PTGS for generating transgenic resistance to AYVV and MYSV, respectively, a construct intended to induce PTGS for generating transgenic resistance to AYVV was also constructed as a control. For this purpose, the IGR fragment of AYVV was amplified with the primer pair P-IGR-Xba I/M-IGR-Xma I by PCR and introduced into pK2T binary vector at Xba I/Xma I sites to generate pK2T-IGR.

A hairpin RNA construct was also used as a control for generating transgenic resistance to AYVV by the PTGS approach. The hairpin fragment of AYVV IGR in pEN-int-hpIGR was amplified by PCR with the primer pair P-IGR-Xba I/M-spacer-Xba I, and introduced into PK2T-IGR via Xba I/Xba I sites to generate the pK2T-hpIGR.

Furthermore, an untranslatable construct was used as a control for generating transgenic resistance to MYSV by the PTGS approach. The untranslatable MYSV-NP coding sequence, with two stop codons at the 5' end, was amplified by PCR with the primer pair P-MYSV-Xba I/M-MYSV-Xma I from pTOPO-MYSV and introduced into pK2T binary vector via Xba I/Xma I sites to generate pK2T-MYSV-NP.

A positive control as showed in SEQ ID NO: 5 was constructed for confirmation of the splicing of the At3947160 intron. The intron fragment released from Nde I and Nhe I sites from pEN-intron, was subsequently inserted into the pK2T-MYSV-NP vector to generate pK2T-MY-intron-NP.

Figure 1:
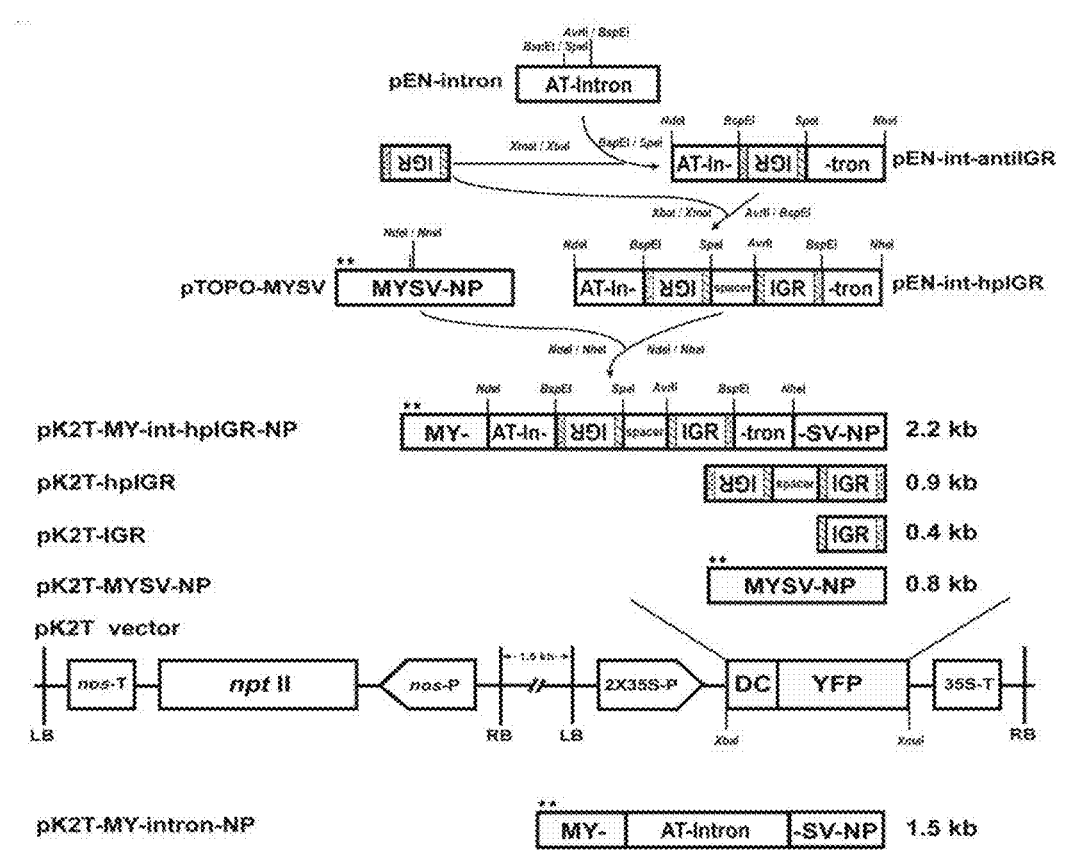

Please refer to FIG. 1, which is a schematic diagram of constructions of the present invention.

A two-T-DNA binary vector system including a nptII selection marker gene in one T-DNA border sequences and a target gene in the other T-DNA border sequences, the two-T-DNA binary vector is constructed for generation of marker-free transgenic plants. To induce RdDM, the target gene comprises the int-hpIGR construct as a hairpin structure of IGR of AYVV.

In this invention, the fragment of IGR sequence showed in SEQ ID NO: 1 is the IGR (284 bp) flanked by 54 bp corresponding to N-terminal 18 amino acids of C1 gene and 56 bp corresponding to N-terminal 19 amino acids of V2 gene. Then, the fragment of IGR sequence is linked with the inverted repeat of the same by a 96 bp (nt 142-257 At3947160) spacer to obtain the hpIGR as showed in SEQ ID NO: 2. The C1 gene is coding for viral replication protein which initiates rolling circle replication, and the V2 gene is coding for movement protein of AYVV.

The int-hpIGR construct is inserted into an untranslatable NP sequence (840 bp) of MYSV (as shown in SEQ ID NO: 3), which acted as exonic sequences after splicing, to form the construct MY-int-hpIGR-NP (as shown in SEQ ID NO: 4). After splicing, the MY-int-hpIGR-NP induces transgenic resistance against MYSV based on PTGS mechanism. The constructs of IGR, hpIGR and untranslatable MYSV NP are generated without an inserted intron to confer the transgenic resistance to AYVV regulated by PTGS mechanism.

All these constructs are constructed in the expression cassette of the two-T-DNA binary vector in which the kanamycin selection marker. All of the transgene have their own T-DNA border sequences to form pk2T-MY-int-hpIGR-NP, pk2T-hpIGR, pk2T-IGR, and pk2T-MYSV-NP, and all transgene constructs are separately transferred into *Agrobacterium tumefaciens* strain ABI. Individual constructs are used to transform tobacco (*Nicotiana benthamiana* Domin) plants via agroinfiltration and the corresponding transgenic lines are regenerated.

2. Confirmation of Splicing of MY-int-hpIGR-NP by Reverse Transcription Polymerase Chain Reaction (RT-PCR) in Transformated *N. benthamiana* Plants.

All the pK2T constructs were separately introduced into *A. tumefaciens* strain ABI. Individual colonies of the bacteria carrying each construct were cultured in the LB medium at 28° C. for 16 hours and then subcultured in LB media with 10 mM 2-(N-morpholino) ethanesulfonic acid (MES) and 40 mM acetosyringone up to an $OD_{600}$ of 0.5. The bacteria were then spun down and pellets were resuspended in 10 mM $MgCl_2$ and 150 mM acetosyringone, and kept at room temperature for 3 hours. With a 2 ml syringe without needle, the suspension was infiltrated into the intercellular space of leaves of *N. benthamiana* plants. The infiltrated leaf tissue was conducted to obtain regenerate transgenic plants.

Total RNAs were extracted using TRIzolH reagent (Invitrogen, Carlsbbad, Calif., USA) from tobacco leaf tissues agroinfiltrated with individual constructs of pK2T-MYSV-NP, pK2T-MY-intron-NP and pK2T-MY-int-hpIGR-NP. The first-strand cDNA were synthesized with M-MLV reverse transcriptase using M-MYSV-Xma I primer (Epicentre, Madison, Wis., USA) at 42° C. for one hour. The PCR amplification was performed with Taq DNA polymerase (MDBio Inc., Taipei, Taiwan) using the primers P-MYSV-Xba I and M-MYSV-Xma I to amplify the corresponding MYSV-NP fragment. For confirming the fidelity of the spliced transcript, the RT-PCR amplified fragment from the tissues agroinfiltrated with pK2T-MY-int-hpIGR-NP was sequenced.

Figure 2:
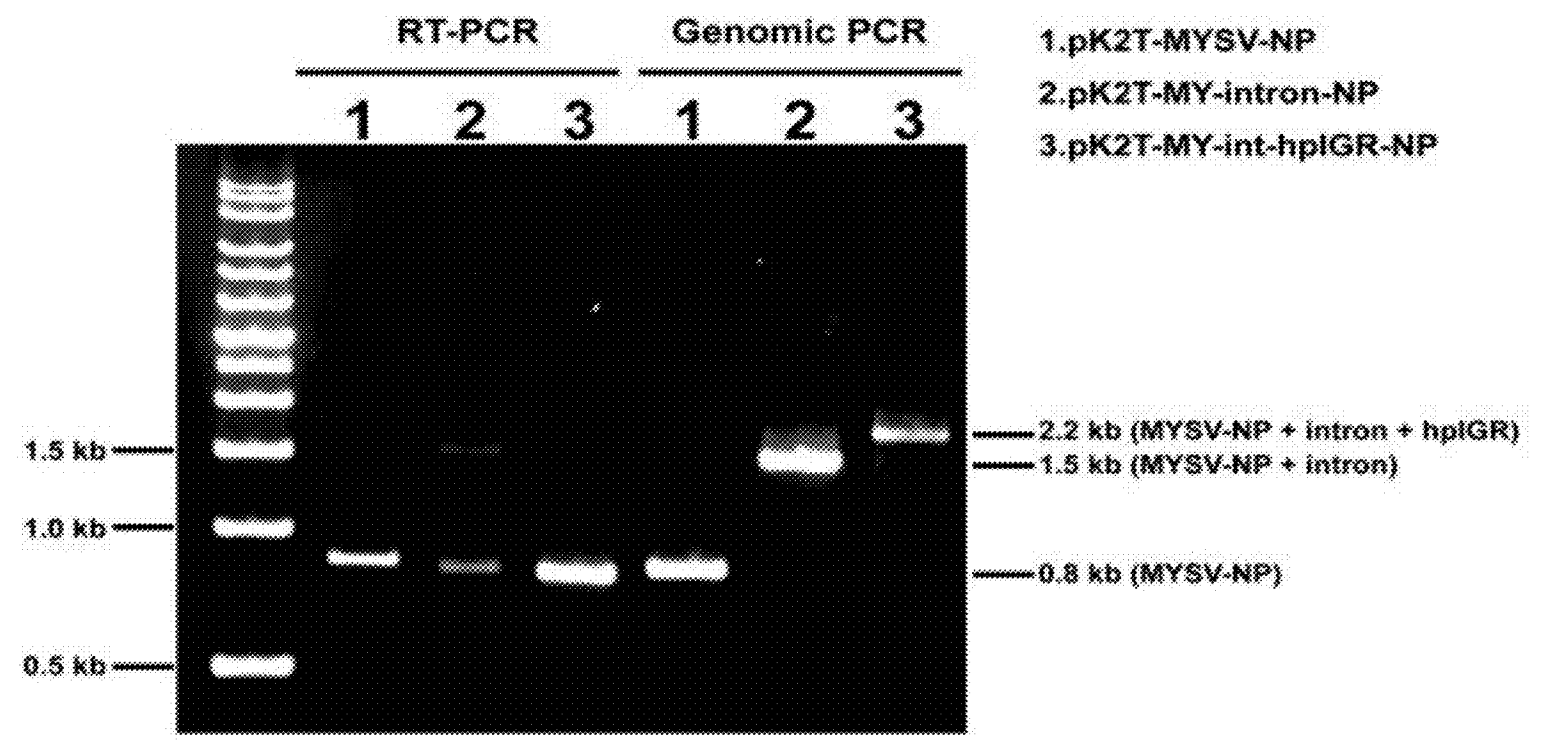

Please refer to FIG. 2, which is an analysis of the splicing of individual constructs in tobacco leaves.

In order to examine whether the hairpin construct is properly processed, total RNAs are extracted from tobacco leaves at 3 days after agroinfiltration with individual constructs. The specific primers P-MYSV-Xba I and M-MYSV-Xma I, which the targeting regions are flanking the intron sequence of MYSV NP gene, are used in RT-PCR analysis to confer the tissues agroinfiltrated with pk2T-MY-intron-NP (an untranslatable MYSV NP with the intron as a positive control) or pk2T-MY-int-hpIGR-NP, and the pK2T-MYSV-NP is used as the control which contains no intron.

The total DNAs, which are extracted from leaf tissues agroinfiltrated with individual constructs of pk2T-MY-intron-NP and pk2T-MY-int-hpIGR-NP, are amplified by PCR using the same primers of RT-PCR analysis as unspliced controls, and the PCR products of 1.5 kb and 2.2 kb are amplified respectively. The result of PCR analysis of pk2T-MYSV-NP, which contains no intron, is amplified 0.8 kb fragment. When the RT-PCR amplified 0.8 kb fragment is sequenced, the result indicated that the intron is spliced at the correct sites of pk2T-MY-int-hpIGR-NP to form the untranslatable MYSV NP in tobacco plants.

3. Evaluation of Resistance to AYVV

The plantlets micropropagated from an individual shoot regenerated after transformation with each construct were considered an individual transgenic line. Rooted shoots of transgenic plantlets of each transgenic line were transplanted onto Florobella (Klasmann-Deilmann, Geeste, Germany) potting compost-sand mix (3:1) in a growth chamber for 4-5 days for hardening, and then they were grown in temperature-controlled conditions (23-28° C.) in a greenhouse for 2 weeks (5-6 leaf stage). The infectious clones used the Rolling Circle Amplification (RCA) products of genome of AYVV was digested and ligated into the Pst I/BamH I site of the binary vector pCAMBIA0380 to generate infectious construct pAYVV. The pAYVV harboring bacteria grown in LB medium containing 50 mg/l kanamycin and 50 mg/l streptomycin at 28° C. for 16 hours was used at an $OD_{600}$ of 0.1. The transgenic plants were injured at the junction of stem and petiole at three places with a needle (23 G, 0.63*25 mm) of a syringe with bacterial suspension. Non-transgenic *N. benthamiana* plants were used as controls. All inoculated plants were kept in a temperature-controlled (23-28° C.) greenhouse and symptom development was monitored daily up to 8 weeks. AYVV infection on all transgenic plants with symptoms was confirmed by PCR assay with P-AYVV-C4/M-AYVV-C4 primers specific to C4 gene.

IGR, hpIGR and MY-int-hpIGR-NP transgenic tobacco lines are obtained and evaluated by challenge inoculation with the infectious construct pAYVV by agroinfection under greenhouse conditions. The results are summarized in Table 2.

TABLE 2

Evaluation of $T_0$ transgenic tobacco lines by agroinfection with Ageratum yellow vein virus (AYVV) under greenhouse conditions

| Line | Total No. of lines. | No. of lines without symptoms at dpa[a] | | | | | | | | Resistance rate (%)[b] |
|---|---|---|---|---|---|---|---|---|---|---|
| | | 10 | 13 | 15 | 17 | 20 | 25 | 30 | 35 | |
| NT | 0 | 0 | 0 | 0 | 0 | 0 | 0 | 0 | 0 | 0 |
| MYSV-NP | 25 | 0 | 0 | 0 | 0 | 0 | 0 | 0 | 0 | 0 |
| IGR | 25 | 5 | 3 | 1 | 0 | 0 | 0 | 0 | 0 | 0 |
| hpIGR | 23 | 7 | 7 | 7 | 2 | 1 | 0 | 0 | 0 | 4 |
| MY-in-hpIGR-NP | 25 | 7 | 7 | 7 | 7 | 7 | 3 | 1 | 0 | 28 |

[a]The testplants(5plants for eachline)are agroinfected with the infectious clone pAYVV.
NT: non-transgenic control; dpa: days post-agroinfection.
[b]No. of lines with resistance/total lines tested, recorded at 20 dpa by symptom development and PCR detection.

Figure 3:
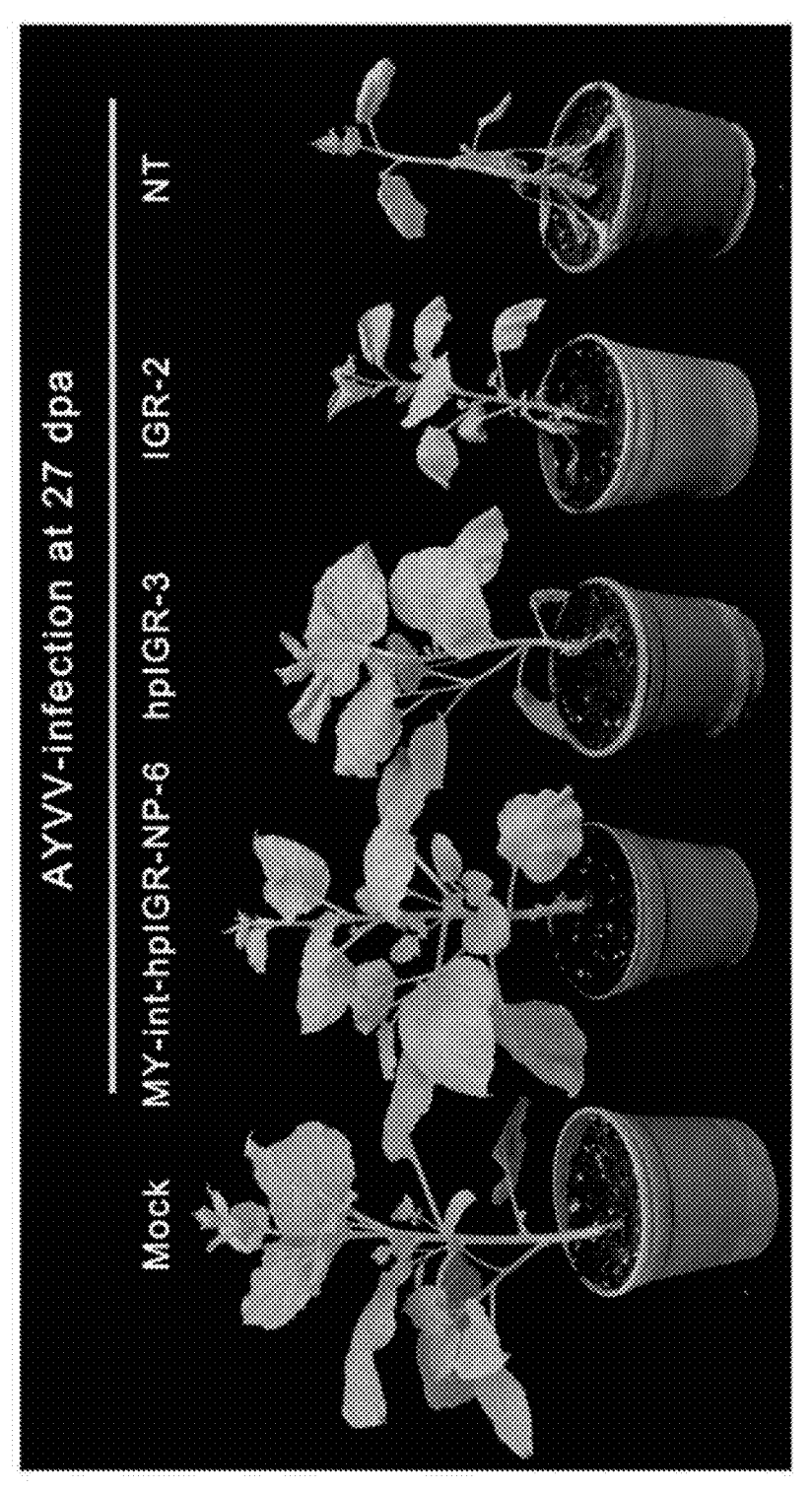

All the non-transgenic plants developed leaf curl symptom at 10 days post-agroinfection (dpa). The delay-type resistant lines are defined as more than 30% individuals developed delay in symptom development as compared to that of the non-transgenic plants. At 20 dpa, 28% of the MY-int-hpIGR-NP lines showed resistance, while only 4% of the hpIGR lines and none (0%) of the IGR lines showed resistance Please refer to FIG. 3, which shows symptom of the individual tobacco plant at 27 days post-agroinfection with the infectious construct pAYVV.

To confirm the symptom of transgenic plants is related with AYVV infection, the specific primers of AYVV C4 gene is used by PCR analysis during the test period of 38 days following inoculation. At 27 dpa, various degrees of leaf curl symptom are observed on leaves of AYVV-inoculated transgenic lines, for example, plants of MY-int-hpIGR-NP-6 line are symptomless in contrast to line hpIGR-3 that showed mild leaf curl symptom and line IGR-2 that showed severe leaf curl symptom. The results indicated that the construct MY-int-hpIGR-NP confers a better degree of transgenic resistance to AYVV than those conferred by the constructs of hpIGR or IGR.

4. Northern Blotting Analysis for siRNA Detection

For small interfering (si) RNA detection, total RNAs of transgenic plant are isolated and separated. The [$\alpha$-$^{32}$P] ATP-labeled probe was prepared from the IGR fragment using Primer-It II random primer labeling kit (Stratagne, LaJolla, Calif.), following manufacturer's instructions. After post-hybridization washing of the filter, autoradiography was performed by mounting an X-ray film (Hyperfilm Mp, Amershan Phamacia Biotech, UK) on the membrane at room temperature.

Please refer to FIG. 4, which shows the detection of the siRNAs accumulation in plant related with AYVV resistant.

The accumulation of siRNA is detected by Northern blotting using an IGR probe. Please refer to FIG. 4, part (a). The result shows that the MY-int-hpIGR-NP-6, hpIGR-3 and IGR-2 transgenic lines, which delay in development of leaf curl symptom respectively showed 21, 11 and 6 days, are observed the siRNA accumulation. Please refer to FIG. 4, part (b), the autoradiograph of a larger gel with longer electrophoresis revealed accumulation of 24-nt siRNA as the dominant siRNA for line MY-int-hpIGR-NP-6, 24-nt and 21-nt siRNAs for line hpIGR-3, and 21-nt siRNA for line IGR-2. The results indicated that the higher degrees of resistance to AYVV in MY-int-hpIGR-NP-6 and hpIGR-7 lines are correlated to the accumulation of 24-nt siRNA.

5. Bisulfite Sequencing Analysis.

To confirm the methylation status of the transgene, bisulfite sequencing was performed with required modifications. The genomic DNA of transgenic tobacco plant was extracted using the Plant Genomic DNA Purification Kit (Genemark, Taichung, Taiwan), and 500 ng of AseI-digested DNA was bisulfite-treated with the EZ DNA Methylation™ kit (Zymo Research, Irvine, Calif., U.S.A.). The bisulfite-treated DNA was amplified by PCR with Platinum Taq DNA Polymerase (Invitrogen, Carlsbad, Calif., U.S.A.). The 247-bp (IGR-247) and the 350-bp (IGR-350) fragments were amplified with the BisP1/BisM1 and BisP2/BisM2 primers from MY-int-hpIGR-NP and hpIGR constructs, respectively. As a positive control for full cytosine conversion, 500 ng of genomic DNA of non-transgenic tobacco was mixed with approximately 40 pg of Ase I-cleaved plasmid DNA. For each sample, the resulted PCR products were directly sequenced three times and the sequences were analyzed using the software Vector NTI Advance 10.3 to assess the frequency of methylation.

Please refer to FIG. 5, which is a physical map of the MY-int-hpIGR-NP transgene, in which the regions analyzed by bisulfite sequencing are indicated.

Genomic DNAs of resistant or susceptible lines carrying transgene MY-int-hpIGR-NP or hpIGR are analyzed by bisulfite sequencing for examining the status of methylation on the transgene. The pMY-int-hpIGR-NP or phpIGR is mixed with genomic DNA of healthy plant and used as controls, and no methylation sequence is observed in PCR products.

The amplified 247-bp (IGR-247) fragment, which reflects the IGR containing the leftward promoter region and 54 bp of the 5' C1 coding sequence, is analyzed. From three independent repeats, the degree of methylation of the IGR sequence from the MY-int-hpIGR-NP resistant lines (lines 6 and 12) reaches an average rate of 92±2%, while that of the MY-int-hpIGR-NP susceptible lines (lines 2 and 19) shows only an average methylation rate of 40±2%. In susceptible lines, the average methylation rate at asymmetric CHH (where H=A, T or G) sites is low as 25±1%, while the average methylation rate of CHH form resistant lines is 91±2%. Methylation did not spread into intron sequence flanking the IGR sequence, as reflected by the results that all cytosines within the intron/spacer are not methylated.

The amplified 350 bp (IGR-350) fragment, which reflects the whole IGR containing the leftward and the rightward promoter regions, 54 bp of 5'-C1 coding region, and the 9 bp of the 5'-V2 coding region, is analyzed, and the degree of methylation of the IGR sequence from resistant lines reaches an average rate of 93±1%, while the susceptible lines shows an average rate of 37±2%. In susceptible lines, methylation rate at asymmetric CHH sites is only 22±3%, while in resistant lines, the average methylation rate of CHH is 91±1%.

The methylation statuses in IGR-247 and IGR-350 fragment of hpIGR lines are also analyzed. The hpIGR transgene in hpIGR-3 resistant line is methylated up to 80-100%, whereas hpIGR-7 susceptible lines show lower methylation rates of 35-40%, especially at asymmetric CHH sites is only 20-30%. This results demonstrate that RdDM derived from the construct MY-int-hpIGR-NP specifically targets at the IGR sequence of the transgenic plant, and the resulted higher levels of methylation are correlated to higher levels of the transgenic resistance to AYVV.

6. Evaluation of Resistance to MYSV

The transgenic tobacco plants (5-6 leaf stage) were also mechanically inoculated with MYSV, and non-transgenic tobacco plants obtained by tissue culture were used as controls. The MYSV inoculum was prepared from virus-infected plants of *N. benthamiana* 8 days after mechanical inoculation, by grinding 1 g leaf tissue with 50 ml 0.01 M potassium phosphate buffer, pH 7.0. The test plants were inoculated by rubbing the carborundum (600 mesh)-dusted first and second fully expanded leaves. Inoculated plants were kept in a temperature-controlled greenhouse (23-28° C.) and symptom development was monitored up to 5 weeks after inoculation. The accumulation of MYSV was assessed by indirect ELISA using the antiserum to the MYSV N protein.

Please refer to FIG. 6, which is a symptom of transgenic MY-int-hpIGR-NP and MYSV-NP lines by mechanical inoculation with MYSV.

Transgenic tobacco lines transformed with individual constructs are evaluated by challenge inoculation with MYSV under greenhouse conditions, and the results are summarized in Table 3. All the infected non-transgenic plants, hpIGR and IGR lines developed symptom of yellow spots and mosaic on upper leaves 8 days post-inoculation (dpi), followed by wilting at 20 dpi. Two MYSV-NP lines show 10 days delay in symptom development and line MYSV-NP-5 do not show any symptoms up to 38 dpi. Three AYVV-resistant MY-int-hpIGR-NP lines show 10 days delay in symptom development, and among them, line MY-int-hpIGR-NP-6 is found to be resistant to MYSV infection at 38 dpi. MYSV accumulation is not detected in lines MYSV-NP-5 and MY-int-hpIGR-NP-6 bp indirect ELISA during 5 to 38 dpi.

TABLE 3

Evaluation of $T_0$ transgenic tobacco lines by mechanical inoculation with Melon yellow spot virus (MYSV) under greenhouse conditions

| Line | Total No. of lines | No. of lines without symptoms at dpa[a] | | | | | | | Resistance rate (%)[b] |
|---|---|---|---|---|---|---|---|---|---|
| | | 8 | 13 | 18 | 23 | 28 | 33 | 38 | |
| NT | 0 | 0 | 0 | 0 | 0 | 0 | 0 | 0 | 0 |
| MYSV-NP | 25 | 3 | 3 | 2 | 1 | 1 | 1 | 1 | 12 |
| IGR | 25 | 0 | 0 | 0 | 0 | 0 | 0 | 0 | 0 |
| hpIGR | 23 | 0 | 0 | 0 | 0 | 0 | 0 | 0 | 0 |
| MY-in-hpIGR-NP | 25 | 5 | 5 | 3 | 1 | 1 | 1 | 1 | 20 |

[a]The test plants (5 plants for each line) are mechanically challenged with MYSV. NT: non-transgenic plants as control, dpi: days post-inoculation.
[b]No. of lines with resistance/total lines tested, as recorded by symptom development and indirect ELISA detection at 13 dpi.

Figure 7:
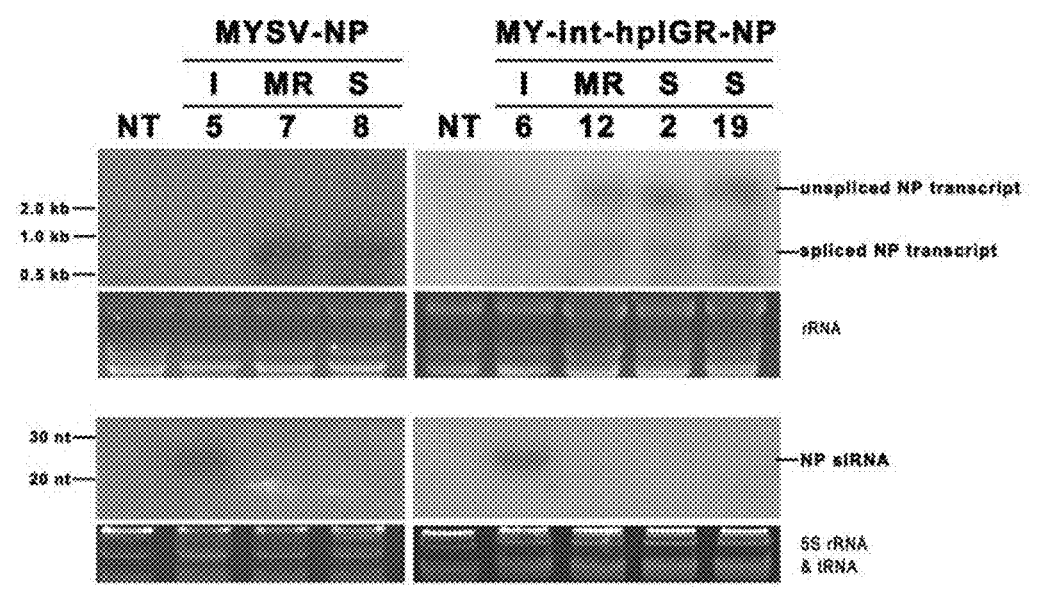

Please refer to FIG. 7, which shows the detection of MYSV-NP transcript and siRNAs in MY-int-hpIGR-NP and MYSV-NP lines.

The MYSV probe used for Northern blotting was amplified by PCR with the primer pairs of P-MYSV-Xba I and M-MYSV-Xma I. The results of Northern blotting analyses for detection of the transgene transcript and siRNA in MYSV-NP and MY-int-hpIGR-NP lines before inoculation. The two completely MYSY-resistant lines, MYSV-NP-5 and MY-int-hpIGR-NP-6 show siRNA signal, but accumulation of transgene transcript was not detected. In contrast, accumulation of transgene transcript in the moderately resistant lines (MYSV-NP-7 and MY-int-hpIGR-NP-12) and susceptible lines (MYSV-NP-8, MY-int-hpIGR-NP-2 and 19) is noticed, but siRNA signal is not detected.

The transcripts of 2.2 kb and 0.8 kb fragments are noticed in these MY-int-hpIGR-NP lines, and are corresponded to the unspliced and spliced forms of the untranslatable NP gene transcript respectively. Such results indicate that the MYSY-resistant in transgenic plant is silenced and responded to the accumulation of NP transcript, and is generated during the accumulation of the transgenic siRNA. That is, the untranslatable NP construct of MY-int-hpIGR-NP-6 line confers complete resistance to MYSV through PTGS mechanism.

7. Southern Blotting Analysis

Fifteen mg of total DNA, extracted as described above, from non-transgenic plants or $T_0$ plant of MY-int-hpIGR-NP transgenic lines, was digested with Ase I that digests the construct once before the transgene sequences. The digested products were separated by electrophoresis on a 0.8% agarose gel, and then transferred to nylon membrane by a POSIBLOT™ pressure blotter (Stratagene, Calif., USA). The DNA bound to the nylon membrane was hybridized with the probe generated from the NP sequence of MY-int-hpIGR-NP construct by PCR amplification using specific primer pair (P-MYSV-Xba I/MYSV-N-350) and labeled with [$\alpha$-$^{32}$P] ATP by the Prime-It II random primer labeling kit (Stratagene, Calif., USA), following manufacturer's instructions. After post-hybridization washing of the filter, autoradiography was performed by mounting an X-ray film (Hyperfilm Mp, Amershan Phamacia Biotech, UK) on the membrane at room temperature.

Figure 8:
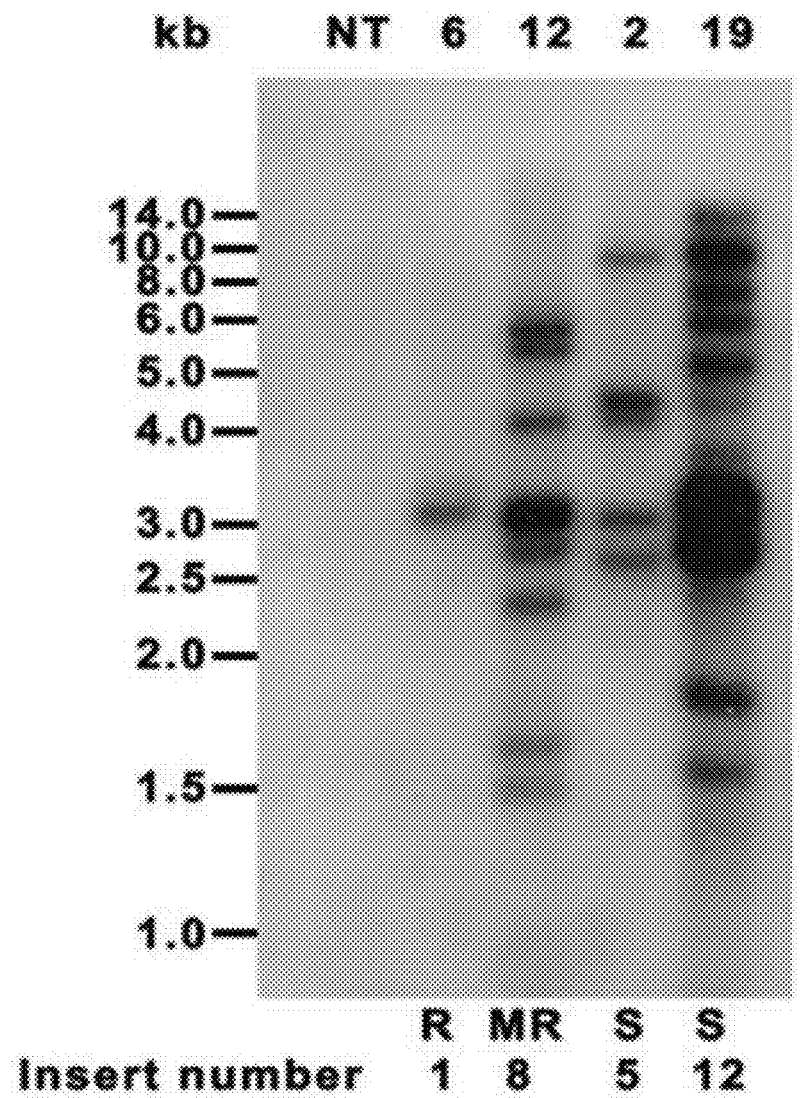
FIG. 8 shows the result of Southern blotting analyses of MY-int-hpIGR-NP MY-int-hpIGR-NP transgenic lines.

Please refer to FIG. 8, which shows the result of Southern blotting analyses of MY-int-hpIGR-NP MY-int-hpIGR-NP transgenic lines.

The MYSV NP probe is used in Southern blotting analysis and the NT plant is used as negative control, the results show that the transgene MY-int-hpIGR-NP is integrated into the genome of the line MY-int-hpIGR-NP-6 at a single locus, while in those of the lines MY-int-pIGR-NP-12, 2 and 19 at eight, five and twelve loci, respectively.

8. Segregation Analyses of the Transgene in $T_1$ and $T_2$ Progenies

The primer pair of MY-int-hpIGR-NP is used in PCR analysis to confer the $T_1$ or $T_2$ segregation and the correlation of AYVV resistance or MYSV resistance. As showed in Table 4, 90 $T_1$ seedlings obtained from the selfing of the AYVV-resistant MY-int-hpIGR-NP-6 are evaluated by agroinfection with AYVV, and 64 of the seedlings are PCR-positive for the transgene MY-int-hpIGR-NP, while the other 26 seedlings are negative, the result also indicate a 3:1 segregation. Ten days after inoculation, 55 resistant plants are symptomless and all of them are PCR-positive for the transgene MY-int-hpIGR-NP, whereas all the other plants display severe symptoms. A total of 23 resistant plants (26%) displayed symptoms during 41-50 dpa. The longer delay in symptom development is apparently due to the homozygotic combination of the single-insert transgene in the $T_1$ population.

Another set of 110 $T_1$ seedlings from the selfing of the line MY-int-hpIGR-NP-6 are evaluated by challenge inoculation with MYSV. As shown in Table 4, 79 of the seedlings are PCR-positive for the transgene, while the other 31 plants are negative, also indicating a 3:1 segregation. When the PCR-positive seedlings are inoculated with MYSV, none of the 79 plants show symptoms, and all of the plants are ELISA negative when they are tested with MYSV NP antiserum at 50 dpi. All the other 31 plants without the transgene displayed severe symptoms within 8 days after inoculation. Thus, the segregation analyses of $T_1$ seedlings indicate that the single-inserted transgene in line MY-int-hpIGR-NP-6 is nuclearly inherited as a single dominant trait, conferring concurrent resistance to both AYVV and MYSV.

TABLE 4

Segregation analyses of the transgene in $T_1$ and $T_2$ progenies of the resistant line MY-int-hpIGR-NP-6 by PCR and challenge inoculation with AYVV and MYSV under greenhouse conditions.

| Virus and transgenic line | No. of seedlings tested | PCR analysis[a] | | No. of plants without symptoms at dpa (AYVV) or dpi (MYSV)[b] | | | | | | Resistance rate at 40 dpa or dpi (%)[c] |
|---|---|---|---|---|---|---|---|---|---|---|
| | | Positive | Negative | 8 | 10 | 20 | 30 | 40 | 50 | |
| AYVV | | | | | | | | | | |
| MY-int-hpIGR-NP-6 ($T_1$) | 90[e] | 64 | 26 | 64 | 55 | 38 | 23 | 23 | 0 | 26 |

TABLE 4-continued

Segregation analyses of the transgene in $T_1$ and $T_2$ progenies of the resistant line MY-int-hpIGR-NP-6 by PCR and challenge inoculation with AYVV and MYSV under greenhouse conditions.

| Virus and transgenic line | No. of seedlings tested | PCR analysis[a] | | No. of plants without symptoms at dpa (AYVV) or dpi (MYSV)[b] | | | | | | Resistance rate at 40 dpa or dpi (%)[c] |
|---|---|---|---|---|---|---|---|---|---|---|
| | | Positive | Negative | 8 | 10 | 20 | 30 | 40 | 50 | |
| MY-int-hpIGR-NP-6 (T$_2$)[d] | 50 | 50 | 0 | 50 | 50 | 50 | 38 | 35 | 0 | 70 |
| NT | 30 | 0 | 30 | 30 | 0 | 0 | 0 | 0 | 0 | 0 |
| MYSV | | | | | | | | | | |
| MY-int-hpIGR-NP-6 (T$_1$) | 110[f] | 79 | 31 | 79 | 79 | 79 | 79 | 79 | 79 | 72 |
| MY-int-hpIGR-NP-6 (T$_2$)[d] | 40 | 40 | 0 | 40 | 40 | 40 | 40 | 40 | 40 | 100 |
| NT | 30 | 0 | 30 | 0 | 0 | 0 | 0 | 0 | 0 | 0 |

[a] The $T_1$ and $T_2$ seedlings were detected by PCR with primers specific to the transgene MY-int-hpIGR-NP.
[b] The AYVV-infected non-transgenic plants developed leaf curl symptom 10 days post-agroinfection (dpa) and MYSV-inoculated plants showed leaf yellow spots 8 days post-inoculation (dpi).
[c] No. plants without symptoms/total plants tested.
[d] MY-int-hpIGR-NP-6 (T$_2$): the progeny from selfing of a $T_1$ plants (MY-int-hpIGR-NP-6-4) of the resistant line MY-int-hpIGR-NP-6.
[e] $x^2 = 0.39$ and $P = 0.73$, in accordance with a 3:1 ratio.
[f] $x^2 = 0.44$ and $P = 0.59$, in accordance with a 3:1 ratio.

Figure 9:
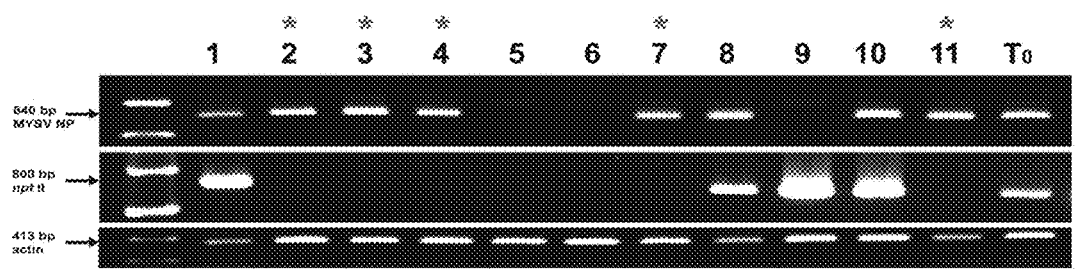
FIG. 9 shows the result for selecting the marker-free seedlings of $T_1$ progeny after selfing of a $T_0$ plant of line MY-int-hpIGR-NP-6. The marked (*) $T_1$ seedlings are PCR-positive for MYSV-NP, but PCR-negative for npt II.

Please refer to FIG. 9, which shows the result for selecting the marker-free seedlings of $T_1$ progeny after selfing of a $T_0$ plant of line MY-int-hpIGR-NP-6.

The $T_1$ seedlings are analyzed by PCR with MYSV-NP and npt II specific primers. The marked (*) $T_1$ seedlings are PCR-positive for MYSV-NP, but PCR-negative for npt II. Please refer to Table 4 again, The $T_1$ seedlings from the selfing of a $T_0$ plant of line MY-int-hpIGR-NP-6 are analyzed by PCR with MYSV-NP and npt II specific primers. Individual plants PCR-positive for the transgene MY-int-hpIGR-NP, but PCR-negative for npt II selection marker, are selected to obtain $T_1$ progeny of marker-free transgenic plants. When a total of 50 marker-free $T_2$ plants, generated from the selfing of a selected $T_1$ individual MY-int-hpIGR-NP-6-4, are tested by PCR with MY-int-hpIGR-NP specific primers, all of them showed the presence of the transgene. The result indicates that the $T_1$ individual MY-int-hpIGR-NP-6-4 and its $T_2$ progeny carry the homozygotic transgene.

When these $T_2$ homozygous plants are agroinfected with AYVV, 15 plants showed 10-30 days delay in symptom development, and the other 35 plants (70%) developed leaf curl symptom during 41-50 dpa. In comparison, all hemizygote of $T_0$ plants showed symptoms within 31 dpa. AYVV infection in all the plants with symptoms is confirmed by PCR detection. When another set of 40 $T_2$ homozygotic plants were mechanically challenged with MYSV, all of them showed complete resistance to MYSV at 50 dpi, as reflected by lack of symptom and MYSV ELISA negativity. The results indicated that the homozygotic $T_2$ plants inherit complete resistance to MYSV from the $T_0$ plants of the line MY-int-hpIGR-NP-6.

Taken all together, the results demonstrate that npt II selection marker gene is completely removed in individuals of $T_2$ progeny of the resistant line MY-int-hpIGR-NP-6, in which the transgene is inherited as a single dominant nuclear trait conferring double resistance to both AYVV and MYSV. Furthermore, the homozygotic MY-int-hpIGR-NP-6 $T_1$ and $T_2$ plants confer higher degrees of resistance to AYVV than the hemizygotic $T_0$ and $T_1$ plants, and are reflected in longer delay for symptom development. The longer delay-type resistance of homozygotic MY-int-hpIGR-NP-6 plants implies the effectiveness of MY-int-hpIGR-NP construct in economically important short-term crops.

On the other hand, a transgenic tomato with MY-int-hpIGR-NP has obtained, and the transgenic tomato also is conferred to have resistant against the tospovirus MYSV and the begomovirus AYVV, that is, the recombinant construct of the present invention can be used in crops.

The present invention has been described with some preferred embodiments thereof and it is understood that many changes and modifications in the described embodiments can be carried out without departing from the scope and the spirit of the invention that is intended to be limited only by the appended claims.

What is claimed is:

1. A recombinant construct for providing resistance against a DNA virus and an RNA virus to a plant, comprising:
   an intron, comprising a fragment of an intergenic sequence from a flanking sequence in a promoter of the DNA virus, a spacer sequence and an antisense sequence of the fragment of the intergenic sequence, the spacer sequence linked between the fragment of the intergenic sequence and the antisense sequence of the fragment of the intergenic sequence; and
   an exon, the intron being inserted in the exon, and the exon comprising at least a fragment of a nucleocapsid protein gene of the RNA virus, and the nucleocapsid protein gene comprising at least a stop codon at the 5' end;
   wherein the DNA virus is Ageratum yellow vein virus, wherein the RNA virus is Melon yellow sport virus, and wherein the fragment of the intergenic sequence consists of the sequence of SEQ ID NO: 1, and the intron comprises the sequence of SEQ ID NO: 2.

2. The recombinant construct of claim 1, wherein the nucleocapsid protein gene comprises at least two stop codons at the 5' end.

3. A binary vector containing a first control sequence, a second control sequence, and the recombinant construct of claim 1, wherein the intron and the exon of the recombinant construct are operably linked to the first control sequence.

4. The binary vector of claim 3, wherein the first control sequence contains a promoter and a terminator, and the intron and the exon are located between the promoter and the terminator, and no selectable marker gene exists in the first control sequence.

5. The binary vector of claim 3, wherein the promoter of the binary vector comprises a Cauliflower Mosaic Virus 35S promoter, a Cauliflower mosaic virus double 35S promoter or an ubiquitin promoter.

6. A recombinant microorganism prepared by transforming a microorganism with the recombinant construct of claim 1.

7. The recombinant microorganism of claim 6, wherein the microorganism comprises disarmed *Agrobacterium tumefaciens*.

8. A recombinant plant cell with resistance against a DNA virus and an RNA virus, comprising a genome comprising the recombinant construct of claim 1, wherein the DNA virus is Ageratum yellow vein virus, and wherein the RNA virus is Melon yellow sport virus.

9. The recombinant plant cell of claim 8, wherein the recombinant plant cell is free of a marker gene selected from a group consisting of an antibiotic resistance gene, an herbicide resistant gene and a fluorescent protein gene.

10. A method of providing a plant with resistance against a DNA virus and an RNA virus, comprising a step of introducing the recombinant construct of claim 1 into a plant or plant part, wherein a siRNA is generated from the intron of the recombinant construct, to induce RNA-directed DNA methylation in the promoter of the DNA virus to provide the resistance against the DNA virus in the plant;

wherein the exon of the recombinant construct is expressed in a transcript but not translationally expressed in cytoplasm, and induce the post-transcriptional gene silencing to provide the resistance against the RNA virus in plant, wherein the DNA virus is Ageratum yellow vein virus, and wherein the RNA virus is Melon yellow sport virus.

11. The method of claim 10, further comprising:

introducing the recombinant construct into an *Agrobacterium* sp. to obtain a recombinant *Agrobacterium* sp.; and infecting the plant or plant part with the recombinant *Agrobacterium* sp. to obtain a plant having the recombinant construct.

\* \* \* \* \*

SEQUENCE LISTING

<160> NUMBER OF SEQ ID NOS: 29

<210> SEQ ID NO 1
<211> LENGTH: 394
<212> TYPE: DNA
<213> ORGANISM: Ageratum yellow vein virus
<220> FEATURE:
<221> NAME/KEY: Intron
<222> LOCATION: (1)..(394)

<400> SEQUENCE: 1

```
ataagtgagg aaataatttt tggcatttat tttaaatggt cttggaggag ccattgactt    60
ggtcaatcgg tgtctctact aatgctctag caatcggtgt actggagtcc tatatatagt   120
tagacaccaa atggcaatta ttgtaatttt gaaaagaaat tcatacttta atttgaaatc   180
caaaagcggc catccgtata atattaccgg atggccgcga ttttttttt aaagtggtcc    240
ctaccacgaa caaaaatccc ccactcagaa cgctccctca aagttaaatt attaagtggt   300
cccctattta tacttattct ccaagtatta ttttaaacat gtgggatcct cttttgaacg   360
agtttcctga aactgttcac ggttttaggt gtat                               394
```

<210> SEQ ID NO 2
<211> LENGTH: 889
<212> TYPE: DNA
<213> ORGANISM: Artificial Sequence
<220> FEATURE:
<223> OTHER INFORMATION: hpIGR
<220> FEATURE:
<221> NAME/KEY: Intron
<222> LOCATION: (1)..(889)

<400> SEQUENCE: 2

```
atacacctaa aaccgtgaac agtttcagga aactcgttca aaagaggatc ccacatgttt    60
aaataatac ttggagaata agtataaata ggggaccact taataattta actttgaggg    120
agcgttctga gtgggggatt tttgttcgtg gtagggacca ctttaaaaaa aaaatcgcgg   180
ccatccggta atattatacg gatggccgct tttggatttc aaattaaagt atgaatttct   240
tttcaaaatt acaataattg ccatttggtg tctaactata tataggactc cagtacaccg   300
attgctagag cattagtaga gacaccgatt gaccaagtca atggctcctc caagaccatt   360
taaaataaat gccaaaaatt atttcctcac ttatctagta ggtcttgtcc aacgaattgg   420
gtgatgaagt cattttagg tagtcttgtc ctagtttgag tgttgactct tgaagctgaa    480
caaagcctag tctagataag tgaggaaata attttttggca tttattttaa atggtcttgg   540
aggagccatt gacttggtca atcggtgtct ctactaatgc tctagcaatc ggtgtactgg   600
agtcctatat atagttagac accaaatggc aattattgta atttttgaaaa gaaattcata   660
ctttaatttg aaatccaaaa gcggccatcc gtataatatt accggatggc cgcgattttt   720
tttttaaagt ggtccctacc acgaacaaaa atcccccact cagaacgctc cctcaaagtt   780
aaattattaa gtggtcccct atttatactt attctccaag tattatttta aacatgtggg   840
atcctctttt gaacgagttt cctgaaactg ttcacggttt taggtgtat               889
```

<210> SEQ ID NO 3
<211> LENGTH: 840
<212> TYPE: DNA
<213> ORGANISM: Artificial Sequence
<220> FEATURE:
<223> OTHER INFORMATION: untranslatable MYSV-NP
<220> FEATURE:
<221> NAME/KEY: exon
<222> LOCATION: (1)..(840)

<400> SEQUENCE: 3

```
atg taa taa gtt act aag ctg aca aag gag aaa att caa gaa ctt ctt    48
Met     Val Thr Lys Leu Thr Lys Glu Lys Ile Gln Glu Leu Leu
1                5                  10 agt ggt ggg aag tcg gaa gtt gaa ata gaa aca gag gaa tca act gaa    96
Ser Gly Gly Lys Ser Glu Val Glu Ile Glu Thr Glu Glu Ser Thr Glu
 15              20                  25                  30
```

```
gga ttt aac ttc cat tca ttc ttt gcg gat gtg aga gat gag gtg aaa      144
Gly Phe Asn Phe His Ser Phe Phe Ala Asp Val Arg Asp Glu Val Lys
            35                  40                  45 tta aat tat aat aat ggt ata aca att ctg aaa agc aga aag caa gtt      192
Leu Asn Tyr Asn Asn Gly Ile Thr Ile Leu Lys Ser Arg Lys Gln Val
        50                  55                  60 tat gca gct tgc aaa tct ggc aac tac aag ttt tgc ggg aaa aag ata      240
Tyr Ala Ala Cys Lys Ser Gly Asn Tyr Lys Phe Cys Gly Lys Lys Ile
                65                  70                  75 gtt gca tct ggg gat aat gtt ggt cct aat gat tgg aca ttt aaa aga      288
Val Ala Ser Gly Asp Asn Val Gly Pro Asn Asp Trp Thr Phe Lys Arg
            80                  85                  90 act gaa gct gtt atc aga act ttg atg atc agc att gca gaa aag aca      336
Thr Glu Ala Val Ile Arg Thr Leu Met Ile Ser Ile Ala Glu Lys Thr
95                  100                 105                 110 gag aat gaa gaa gaa aag cag aaa atg tat gag aaa gcc atg cag ctt      384
Glu Asn Glu Glu Glu Lys Gln Lys Met Tyr Glu Lys Ala Met Gln Leu
                115                 120                 125 cca ttg gtt gct gca tac ggt tta act gtg cct gca aag ttt gac atg      432
Pro Leu Val Ala Ala Tyr Gly Leu Thr Val Pro Ala Lys Phe Asp Met
            130                 135                 140 aca gct ttg aga tta atg cta tgc att gga gga cct ctg tct ttg ctt      480
Thr Ala Leu Arg Leu Met Leu Cys Ile Gly Gly Pro Leu Ser Leu Leu
        145                 150                 155 gct agt ctg cat tcg ctc tgc cct gtt gtc ctg cct ttg gcc tat ttt      528
Ala Ser Leu His Ser Leu Cys Pro Val Val Leu Pro Leu Ala Tyr Phe
                160                 165                 170 cag aat gtc aag aaa gag caa tta gga ata aag aat ttc tct aca tat      576
Gln Asn Val Lys Lys Glu Gln Leu Gly Ile Lys Asn Phe Ser Thr Tyr
175                 180                 185                 190 gag cag atc tgc aaa att gct cgc gtt atg tct gct agc aat atg acc      624
Glu Gln Ile Cys Lys Ile Ala Arg Val Met Ser Ala Ser Asn Met Thr
                195                 200                 205 ttc aag aaa gaa ttt gat gaa ctt ttc aaa agt tgt gtg aaa atc ttg      672
Phe Lys Lys Glu Phe Asp Glu Leu Phe Lys Ser Cys Val Lys Ile Leu
            210                 215                 220 gct gac tgc aaa cca gga aca acc agt ggc ata tcc ctg aag att tat      720
Ala Asp Cys Lys Pro Gly Thr Thr Ser Gly Ile Ser Leu Lys Ile Tyr
        225                 230                 235 aat gaa cag gtg caa ttc atg gaa caa gct ttc aaa tcc tct ctt gta      768
Asn Glu Gln Val Gln Phe Met Glu Gln Ala Phe Lys Ser Ser Leu Val
                240                 245                 250 gtt gat gga atg ggt gag agc tct tct aag agt aaa gct tct tct tcc      816
Val Asp Gly Met Gly Glu Ser Ser Ser Lys Ser Lys Ala Ser Ser Ser
255                 260                 265                 270 aga gct aag tcc att gaa gtt taa                                      840
Arg Ala Lys Ser Ile Glu Val
                275
```

<210> SEQ ID NO 4
<211> LENGTH: 2260
<212> TYPE: DNA
<213> ORGANISM: Artificial Sequence
<220> FEATURE:
<223> OTHER INFORMATION: MY-int-hpIGR-NP

<400> SEQUENCE: 4

```
atgtaataag ttactaagct gacaaaggag aaaattcaag aacttcttag tggtgggaag    60
tcggaagttg aaatagaaac agaggaatca actgaaggat ttaacttcca ttcattcttt   120
gcggatgtga gagatgaggt gaaattaaat tataataatg gtataacaat tctgaaaagc   180
```

```
agaaagcaag tttatgcagc ttgcaaatct ggcaactaca agttttgcgg gaaaaagata    240
gttgcatctg gggataatgt tggtcctaat gattggacat ttaaaagaac tgaagctgtt    300
atcagaactt tgatgatcag cattgcagaa aagacagaga atgaagaaga aaagcagaaa    360
atgtatgaga aagccatgca gcttccattg gttgctgcat acggtttaac tgtgcctgca    420
aagtttgaca tgacagcttt gagattaatg ctatgcattg gaggacctct gtctttgctt    480
gctagtctgc attcgctctg ccctgttgtc ctgcctttgg cctattttca gaatgtcaag    540
aaagagcaat taggaataaa gaatttctct acatatgtaa gcctctcaaa tttgattcct    600
tttttctttg ttcattttgg agttttctct gtttttgtta tctaaagtta cgatttttat    660
ttctttctgg gtggaaaaaa tctatctttt tggtttaagt gggtttccgg gcatacacct    720
aaaaccgtga acagtttcag gaaactcgtt caaaagagga tcccacatgt ttaaaataat    780
acttggagaa taagtataaa taggggacca cttaataatt taactttgag ggagcgttct    840
gagtggggga ttttttgttcg tggtagggac cactttaaaa aaaaaatcgc ggccatccgg    900
taatattata cggatggccg cttttggatt tcaaattaaa gtatgaattt cttttcaaaa    960
ttacaataat tgccatttgg tgtctaacta tatataggac tccagtacac cgattgctag   1020
agcattagta gagacaccga ttgaccaagt caatggctcc tccaagacca tttaaaataa   1080
atgccaaaaa ttatttcctc acttatctag taggtcttgt ccaacgaatt gggtgatgaa   1140 gtcatttta ggtagtcttg tcctagtttg agtgttgact cttgaagctg aacaaagcct   1200
agataagtga ggaaataatt tttggcattt attttaaatg gtcttggagg agccattgac   1260
ttggtcaatc ggtgtctcta ctaatgctct agcaatcggt gtactggagt cctatatata   1320
gttagacacc aaatggcaat tattgtaatt ttgaaaagaa attcatactt taatttgaaa   1380
tccaaaagcg gccatccgta taatattacc ggatggccgc gatttttttt ttaaagtggt   1440
ccctaccacg aacaaaaatc ccccactcag aacgctccct caaagttaaa ttattaagtg   1500
gtcccctatt tatacttatt ctccaagtat tattttaaac atgtgggatc ctcttttgaa   1560
cgagtttcct gaaactgttc acggttttag gtgtatgccc ggatgatctc agaggaaact   1620
gtgtttgtct gaaatgatca aatatttgaa agctaaaacc tttatttgat ttgatttctg   1680
atggtaatct agttgagtta ggaagttcta tgtctaaaag gtgaatgttt tggtgagttt   1740
cttaatcaat ttagacatct gaggatgctt gattaaatca aactttgatc tttgaagctg   1800
aaaatgtgtt tctgcaatga tcaagaggtg tacttgtgat gctatcttta agttcctcac   1860
ttccatgcat ctcaatggtg cattgatcaa ttgcttctgt tgtttataat ctctgtgatt   1920
cgttcaatac attgaatgat gaattttgtt atgtttgtgt tttttcatca agtgatgttg   1980
ttatggtgct tatgaacatt gtcacttgtt tctcctctgt gaattaacag ctagcaatat   2040
gaccttcaag aaagaatttg atgaactttt caaagttgt gtgaaaatct ggctgactg   2100 caaaccagga acaaccagtg gcatatccct gaagatttat aatgaacagg tgcaattcat   2160
ggaacaagct ttcaaatcct ctcttgtagt tgatggaatg ggtgagagct cttctaagag   2220
taaagcttct tcttccagag ctaagtccat tgaagtttaa                         2260

<210> SEQ ID NO 5
<211> LENGTH: 1472
<212> TYPE: DNA
<213> ORGANISM: Artificial Sequence
<220> FEATURE:
<223> OTHER INFORMATION: MY-intron-NP
```

<400> SEQUENCE: 5

```
atgtaataag ttactaagct gacaaaggag aaaattcaag aacttcttag tggtgggaag      60
tcggaagttg aaatagaaac agaggaatca actgaaggat ttaacttcca ttcattcttt     120
gcggatgtga gagatgaggt gaaattaaat tataataatg gtataacaat tctgaaaagc     180
agaaagcaag tttatgcagc ttgcaaatct ggcaactaca agttttgcgg aaaaagata      240
gttgcatctg gggataatgt tggtcctaat gattggacat ttaaaagaac tgaagctgtt     300
atcagaactt tgatgatcag cattgcagaa aagacagaga atgaagaaga aaagcagaaa     360
atgtatgaga aagccatgca gcttccattg gttgctgcat acggtttaac tgtgcctgca     420
aagtttgaca tgacagcttt gagattaatg ctatgcattg gaggacctct gtctttgctt     480
gctagtctgc attcgctctg ccctgttgtc ctgccttttgg cctattttca gaatgtcaag     540
aaagagcaat taggaataaa gaatttctct acatatgtaa gcctctcaaa tttgattcct     600
tttttctttg ttcattttgg agttttctct gttttgtta tctaaagtta cgattttat      660
ttctttctgg gtgaaaaaaa tctatctttt tggtttaagt gggtttccgg aactagtagg     720
tcttgtccaa cgaattgggt gatgaagtca ttttaggta gtcttgtcct agtttgagtg     780
ttgactcttg aagctgaaca aagcctaggt ccggatgatc tcagaggaaa ctgtgtttgt     840
ctgaaatgat caaatatttg aaagctaaaa cctttatttg atttgatttc tgatggtaat     900
ctagttgagt taggaagttc tatgtctaaa aggtgaatgt tttggtgagt ttcttaatca     960
atttagacat ctgaggatgc ttgattaaat caaactttga tctttgaagc tgaaaatgtg    1020
tttctgcaat gatcaagagg tgtacttgtg atgctatctt taagttcctc acttccatgc    1080
atctcaatgg tgcattgatc aattgcttct gttgtttata atctctgtga ttcgttcaat    1140
acattgaatg atgaatttgt ttatgttgt gtttttcat caagtgatgt tgttatggtg      1200
cttatgaaca ttgtcacttg tttctcctct gtgaattaac agctagcaat atgaccttca    1260
agaaagaatt tgatgaactt ttcaaaagtt gtgtgaaaat cttggctgac tgcaaaccag    1320
gaacaaccag tggcatatcc ctgaagattt ataatgaaca ggtgcaattc atggaacaag    1380
ctttcaaatc ctctcttgta gttgatggaa tgggtgagag ctcttctaag agtaaagctt    1440
cttcttccag agctaagtcc attgaagttt aa                                  1472
```

<210> SEQ ID NO 6
<211> LENGTH: 31
<212> TYPE: DNA
<213> ORGANISM: Artificial Sequence
<220> FEATURE:
<223> OTHER INFORMATION: P-AT int-Nde I

<400> SEQUENCE: 6

```
caccatatgt aagcctctca aatttgattc c                                     31
```

<210> SEQ ID NO 7
<211> LENGTH: 28
<212> TYPE: DNA
<213> ORGANISM: Artificial Sequence
<220> FEATURE:
<223> OTHER INFORMATION: M-AT int-Nhe I

<400> SEQUENCE: 7

```
gctagctgtt aattcacaga ggagaaac                                         28
```

<210> SEQ ID NO 8
<211> LENGTH: 39
<212> TYPE: DNA
<213> ORGANISM: Artificial sequence
<220> FEATURE:
<223> OTHER INFORMATION: P-inBsSp

<400> SEQUENCE: 8
ggtttaagtg ggtttccgga actagtaggt cttgtccaa                          39

<210> SEQ ID NO 9
<211> LENGTH: 39
<212> TYPE: DNA
<213> ORGANISM: Artificial Sequence
<220> FEATURE:
<223> OTHER INFORMATION: M-inBsSp

<400> SEQUENCE: 9
ttggacaaga cctactagtt ccggaaaccc acttaaacc                          39

<210> SEQ ID NO 10
<211> LENGTH: 31
<212> TYPE: DNA
<213> ORGANISM: Artificial Sequence
<220> FEATURE:
<223> OTHER INFORMATION: P-IGR-Xba I

<400> SEQUENCE: 10
cacctctaga taagtgagga ataattttt g                                   31

<210> SEQ ID NO 11
<211> LENGTH: 29
<212> TYPE: DNA
<213> ORGANISM: Artificial Sequence
<220> FEATURE:
<223> OTHER INFORMATION: M-IGR-Xma I

<400> SEQUENCE: 11
cccgggcata cacctaaaac cgtgaacag                                     29

<210> SEQ ID NO 12
<211> LENGTH: 40
<212> TYPE: DNA
<213> ORGANISM: Artificial Sequence
<220> FEATURE:
<223> OTHER INFORMATION: P-inAvBs

<400> SEQUENCE: 12
tgaagctgaa caaagcctag gtccggatga tctcagagga                         40

<210> SEQ ID NO 13
<211> LENGTH: 40
<212> TYPE: DNA
<213> ORGANISM: Artificial Sequence
<220> FEATURE:
<223> OTHER INFORMATION: M-inAvBs

<400> SEQUENCE: 13
tcctctgaga tcatccggac ctaggctttg ttcagcttca                         40

<210> SEQ ID NO 14
<211> LENGTH: 39
<212> TYPE: DNA
<213> ORGANISM: Artificial Sequence
<220> FEATURE:
<223> OTHER INFORMATION: P-MYSV-Xba I

<400> SEQUENCE: 14
gtatctagaa tgtaataagt tactaagctg acaaaggag                                  39

<210> SEQ ID NO 15
<211> LENGTH: 29
<212> TYPE: DNA
<213> ORGANISM: Artificial Sequence
<220> FEATURE:
<223> OTHER INFORMATION: M-MYSV-Xma I

<400> SEQUENCE: 15
aggcccgggt taaacttcaa tggacttag                                             29

<210> SEQ ID NO 16
<211> LENGTH: 30
<212> TYPE: DNA
<213> ORGANISM: Artificial Sequence
<220> FEATURE:
<223> OTHER INFORMATION: M-spacer-Xba I

<400> SEQUENCE: 16
ctctctagac taggctttgt tcagcttcaa                                            30

<210> SEQ ID NO 17
<211> LENGTH: 28
<212> TYPE: DNA
<213> ORGANISM: Artificial Sequence
<220> FEATURE:
<223> OTHER INFORMATION: BisP1

<400> SEQUENCE: 17
ggtaatatta tayggatggy ygyttttg                                              28

<210> SEQ ID NO 18
<211> LENGTH: 30
<212> TYPE: DNA
<213> ORGANISM: Artificial Sequence
<220> FEATURE:
<223> OTHER INFORMATION: BisM1

<400> SEQUENCE: 18
ctacctaaaa atracttcat cacccaattc                                            30

<210> SEQ ID NO 19
<211> LENGTH: 26
<212> TYPE: DNA
<213> ORGANISM: Artificial Sequence
<220> FEATURE:
<223> OTHER INFORMATION: BisP2

<400> SEQUENCE: 19
tagataagtg aggaaataat ttttgg                                                26

<210> SEQ ID NO 20
<211> LENGTH: 26
<212> TYPE: DNA
<213> ORGANISM: Artificial Sequence
<220> FEATURE:
<223> OTHER INFORMATION: BisM2

<400> SEQUENCE: 20
atcccacatr tttaaaataa tacttr                                                26

<210> SEQ ID NO 21
<211> LENGTH: 26
<212> TYPE: DNA
<213> ORGANISM: Artificial Sequence
<220> FEATURE:
<223> OTHER INFORMATION: M-MYSV-N-350

<400> SEQUENCE: 21
tcttcttcat tctctgtctt ttctgc                                    26

<210> SEQ ID NO 22
<211> LENGTH: 20
<212> TYPE: DNA
<213> ORGANISM: Artificial Sequence
<220> FEATURE:
<223> OTHER INFORMATION: P-kan

<400> SEQUENCE: 22
actcgtcaag aaggcgatag                                           20

<210> SEQ ID NO 23
<211> LENGTH: 20
<212> TYPE: DNA
<213> ORGANISM: Artificial Sequence
<220> FEATURE:
<223> OTHER INFORMATION: M-kan

<400> SEQUENCE: 23
gcatgattga acaagatgga                                           20

<210> SEQ ID NO 24
<211> LENGTH: 29
<212> TYPE: DNA
<213> ORGANISM: Artificial Sequence
<220> FEATURE:
<223> OTHER INFORMATION: P-AYVV-C4

<400> SEQUENCE: 24
gaacccctga gggagccctc atctccacg                                 29

<210> SEQ ID NO 25
<211> LENGTH: 30
<212> TYPE: DNA
<213> ORGANISM: Artificial Sequence
<220> FEATURE:
<223> OTHER INFORMATION: M-AYVV-C4

<400> SEQUENCE: 25
agggctccct cagggttct gtacattctg                                 30

<210> SEQ ID NO 26
<211> LENGTH: 29
<212> TYPE: DNA
<213> ORGANISM: Artificial Sequence
<220> FEATURE:
<223> OTHER INFORMATION: P-NB-actin-413

<400> SEQUENCE: 26
aactgatgaa gatactcaca gaaagaggc                                 29

<210> SEQ ID NO 27
<211> LENGTH: 29
<212> TYPE: DNA
<213> ORGANISM: Artificial Sequence
<220> FEATURE:
<223> OTHER INFORMATION: M-NB-actin-413

```
<400> SEQUENCE: 27
caggatacgg ggagctaatg cagtaattt                                              29

<210> SEQ ID NO 28
<211> LENGTH: 247
<212> TYPE: DNA
<213> ORGANISM: Artificial Sequence
<220> FEATURE:
<223> OTHER INFORMATION: Synthetic: IGR-247 fragment

<400> SEQUENCE: 28
ggtaatatta tacggatggc cgcttttgga tttcaaatta agtatgaat ttcttttcaa             60 aattacaata attgccattt ggtgtctaac tatatatagg actccagtac accgattgct           120
agagcattag tagagacacc gattgaccaa gtcaatggct cctccaagac catttaaaat           180
aaatgccaaa aattatttcc tcacttatct agtaggtctt gtccaacgaa ttgggtgatg           240
aagtcat                                                                    247

<210> SEQ ID NO 29
<211> LENGTH: 350
<212> TYPE: DNA
<213> ORGANISM: Artificial Sequence
<220> FEATURE:
<223> OTHER INFORMATION: Synthetic: IGR-350 fragment

<400> SEQUENCE: 29
tagataagtg aggaaataat ttttggcatt tattttaaat ggtcttggag gagccattga            60
cttggtcaat cggtgtctct actaatgctc tagcaatcgg tgtactggag tcctatatat          120
agttagacac caaatggcaa ttattgtaat tttgaaaaga aattcatact ttaatttgaa          180
atccaaaagc ggccatccgt ataatattac cggatggccg cgatttttttt tttaaagtgg         240 tccctaccac gaacaaaaat cccccactca gaacgctccc tcaaagttaa attattaagt          300
ggtcccctat ttatacttat tctccaagta ttattttaaa catgtgggat                     350
```